US012582310B1

(12) United States Patent
Padula, II

(10) Patent No.: US 12,582,310 B1
(45) Date of Patent: Mar. 24, 2026

(54) TELESCOPIC OCULAR REFRACTION TEST APPARATUS, SYSTEM, AND METHOD

(71) Applicant: DR RP HOLDINGS, LLC, Louisville, KY (US)

(72) Inventor: William Vincent Padula, II, Killingworth, CT (US)

(73) Assignee: DR RP HOLDINGS, LLC, Louisville, KY (US)

( * ) Notice: Subject to any disclaimer, the term of this patent is extended or adjusted under 35 U.S.C. 154(b) by 0 days.

(21) Appl. No.: 19/186,090

(22) Filed: Apr. 22, 2025

Related U.S. Application Data

(60) Provisional application No. 63/724,596, filed on Nov. 25, 2024.

(51) Int. Cl.
    *A61B 3/103*     (2006.01)
    *A61B 3/00*     (2006.01)
    *A61B 3/032*     (2006.01)

(52) U.S. Cl.
    CPC ............ *A61B 3/103* (2013.01); *A61B 3/0041* (2013.01); *A61B 3/032* (2013.01)

(58) Field of Classification Search
    CPC ........ A61B 3/103; A61B 3/0041; A61B 3/032
    USPC ........................................................ 351/211
    See application file for complete search history.

(56) References Cited

U.S. PATENT DOCUMENTS

| | | | |
|---|---|---|---|
| 5,090,796 A | 2/1992 | Feinbloom | |
| 8,066,376 B2 | 11/2011 | Wang et al. | |
| 8,087,781 B2 | 1/2012 | Kanazawa et al. | |
| 2008/0100803 A1* | 5/2008 | Dick ......................... | A61B 3/14 |
| | | | 351/212 |
| 2010/0201944 A1* | 8/2010 | Lewis ...................... | A61B 3/14 |
| | | | 351/246 |
| 2015/0374233 A1* | 12/2015 | Zhang ...................... | A61B 3/14 |
| | | | 351/246 |
| 2018/0249151 A1* | 8/2018 | Freeman ................ | G16H 40/63 |
| 2018/0263488 A1 | 9/2018 | Pamplona et al. | |
| 2018/0279872 A1* | 10/2018 | Okamoto ............... | A61B 3/102 |
| 2020/0069174 A1* | 3/2020 | Marin .................... | A61B 3/032 |
| 2020/0409153 A1 | 12/2020 | Padula et al. | |
| 2023/0104168 A1* | 4/2023 | Altal ......................... | G06T 3/40 |
| | | | 351/209 |
| 2023/0225610 A1 | 7/2023 | Lutz et al. | |
| 2023/0309825 A1* | 10/2023 | Takii ...................... | A61B 3/103 |
| | | | 351/221 |

FOREIGN PATENT DOCUMENTS

| | | |
|---|---|---|
| CN | 214017504 | 8/2021 |
| CN | 219480055 | 8/2023 |

OTHER PUBLICATIONS

Greene et al.; "Telescope Glasses For Low Vision: When, Why, How And More"; Low Vision Optometry of Southern California; Oct. 11, 2024.

(Continued)

*Primary Examiner* — Mohammed A Hasan
(74) *Attorney, Agent, or Firm* — GrayRobinson, P.A.

(57) ABSTRACT

A telescopic ocular refraction test system includes a display that displays a vision testing image. The system includes a telescope configured to be positioned in front of an eye of a patient for viewing the vision testing image through the telescope. The system also includes a control system that determines a vision correction parameter based on a position of a focus adjustment device that focuses the telescope.

48 Claims, 22 Drawing Sheets

(56) References Cited

OTHER PUBLICATIONS

Vasconcelos et al.; "Low Vision Aids"; Low Vision Aids—
American Academy of Ophthalmology, Knights Templar Eye Foun-
dation, Pediatirc Ophthalmology Education Center; Nov. 24, 2015.
PCT/US2025/025776 International Search Report and the Written
Opinion of the International Searching Authority dated Jun. 12,
2025, 14 pages.

* cited by examiner

100 ↴

102

ADJUSTING A FOCUS OF A TELESCOPE THROUGH WHICH A VISION TESTING IMAGE IS VISIBLE TO A PATIENT BY MOVING A FOCUS ADJUSTMENT DEVICE TO A POSITION AT WHICH THE VISION TESTING IMAGE IS IN FOCUS TO THE PATIENT

104

DETERMINING A VISION CORRECTION PARAMETER FOR THE PATIENT BASED ON THE POSITION OF THE FOCUS ADJUSTMENT DEVICE

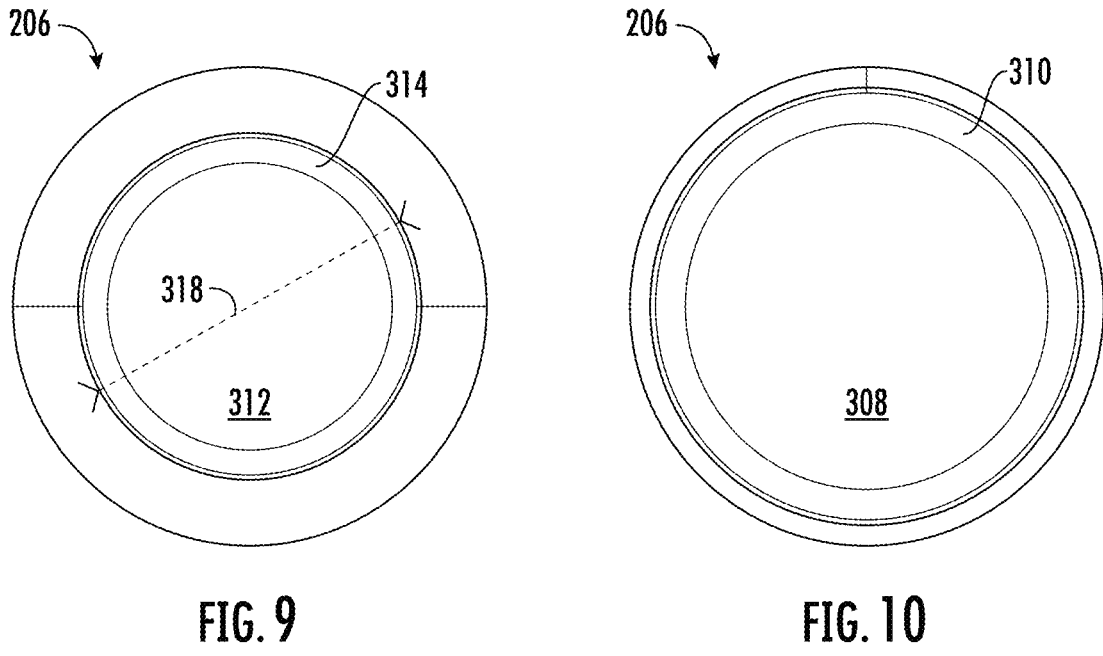
FIG. 9                                FIG. 10
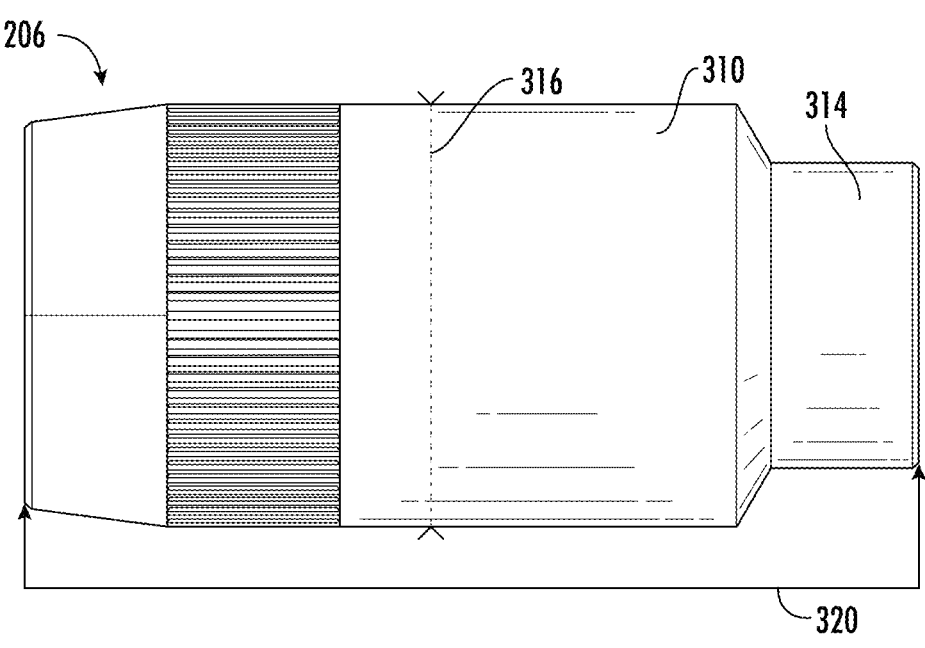
FIG. 11

225

TELESCOPIC OCULAR REFRACTION TEST APPARATUS, SYSTEM, AND METHOD

CROSS-REFERENCE TO RELATED APPLICATION

This claims the benefit of priority from provisional Application No. 63/724,596, filed Nov. 25, 2024, which is incorporated by reference in its entirety.

FIELD

This relates to the field of vision testing and, more particularly, to ocular refraction testing.

BACKGROUND

For people with normal vision, an objective refraction measurement is performed with an auto-refractor, which is refined by a subjective refraction measurement that enables the patient to choose the lenses that provide the best resolution or visual acuity to correct hyperopia, myopia, and astigmatism. Unfortunately, refraction measurements are often not performed for low-vision patients because the patient's vision impairment is primarily the result of underlying ocular disease, not defective refraction.

Ophthalmologists and optometrists have difficulty performing refraction measurements on low vision patients. A low vision patient who has, for example, macular degeneration or glaucoma, often has a central vision loss, which interferes with the patient's ability to perform the subjective refraction measurement. Trial frame refraction can be helpful, but takes a considerable amount of time, and it is difficult for the patient to discern differences between lens choices.

People with vision impairment may also have an uncorrected refractive error that further reduces their visual acuity. For example, if a person has macular degeneration and myopia causing reduced acuity, the reduced acuity may be improved with the refractive lens correction. The acuity of a person with 20/1000 acuity may be improved to 20/200 acuity or better if the person has a moderate to high amount of myopia.

BRIEF SUMMARY

These problems with refraction testing of low vision patients are overcome by the telescopic ocular refraction test apparatus, system, and method described here. The telescopic ocular refraction test apparatus, system, and method can advantageously be used to perform refraction measurements any patient in need of refraction testing, and especially on low vision patients.

An example of the telescopic ocular refraction test system includes a display that displays a vision testing image. The system includes a telescope configured to be positioned in front of an eye of a patient for viewing the vision testing image through the telescope. The system also includes a control system that determines a vision correction parameter based on a position of a focus adjustment device that focuses the telescope.

The system may also include one or more of the following features.

The vision testing image may be a visual acuity chart.

The vision testing image may be a pattern frequency chart.

The vision correction parameter may be at least one parameter selected from the group consisting of sphere power, cylinder power, and cylinder axis.

The telescope may be a Galilean telescope.

The telescope may have a magnification of 1-12.

The eye of the patient may be 5-30 feet from the vision testing image.

The focus adjustment device may manually focus the telescope.

The focus adjustment device may automatically focus the telescope in response to an input signal from the control system.

The position of the focus adjustment device may be calibrated to correspond to a vision correction prescription.

The control system may control the position of the focus adjustment device in response to patient input. The control system may calculate a vision correction prescription for the patient based on the position at which the patient input corresponds to the patient having a highest acuity view of the vision testing image.

An example of a method includes adjusting a focus of a telescope through which a vision testing image is visible to a patient. This is done by moving a focus adjustment device of the telescope to a position at which the vision testing image is in focus to the patient. The method further includes determining a vision correction parameter for the patient based on the position of the focus adjustment device.

The method may also include one or more of the following features.

The patient may have 20/70 or lower uncorrected visual acuity.

The vision testing image may be a visual acuity chart.

The vision testing image may be a pattern frequency chart.

The vision correction parameter may be at least one parameter selected from the group consisting of sphere power, cylinder power, and cylinder axis.

The telescope may be a Galilean telescope.

The telescope may have a magnification of 1-12.

An eye of the patient may be 5-30 feet from the vision testing image.

Moving the focus adjustment device may include automatically focusing the telescope in response to an input signal from a control system.

The position of the focus adjustment device may be calibrated to correspond to a vision correction prescription.

The control system may change the position of the focus adjustment device in response to patient input and determine the vision correction parameter.

Another example of a telescopic ocular refraction test system includes a telescope with a first end housing an eyepiece and a second end housing an objective lens. The system includes a focus adjustment device that changes a distance between the eyepiece and objective lens to focus the telescope. The system includes a control system that converts a position of the focus adjustment device to a vision correction parameter for a patient that views a vision testing image through the telescope.

The system may also include one or more of the following features.

The system may include a display that displays the vision testing image. The vision testing image may be a visual acuity chart and/or a pattern frequency chart.

The vision correction parameter may be at least one parameter selected from the group consisting of sphere power, cylinder power, and cylinder axis.

The telescope may be a Galilean telescope.

The telescope may have a magnification of 1-12.

An eye of the patient may be 5-30 feet from the vision testing image.

The focus adjustment device may manually focus the telescope.

The focus adjustment device may automatically focus the telescope in response to an input signal from the control system.

The position of the focus adjustment device may be calibrated to correspond to a vision correction prescription.

The control system may control the position of the focus adjustment device in response to patient input and calculate a vision correction prescription for the patient based on the position at which the patient input corresponds to the patient having a highest acuity view of the vision testing image.

The telescopic ocular refraction test apparatus, system, and method may also include any combination of these features.

BRIEF DESCRIPTION OF THE DRAWINGS

FIG. 9 is a rear view of the telescope of FIG. 7.

FIG. 10 is a front view of the telescope of FIG. 7.

FIG. 11 is a right side view of the telescope of FIG. 7, the left side view being a mirror image.

DETAILED DESCRIPTION

Figures 1, 2:
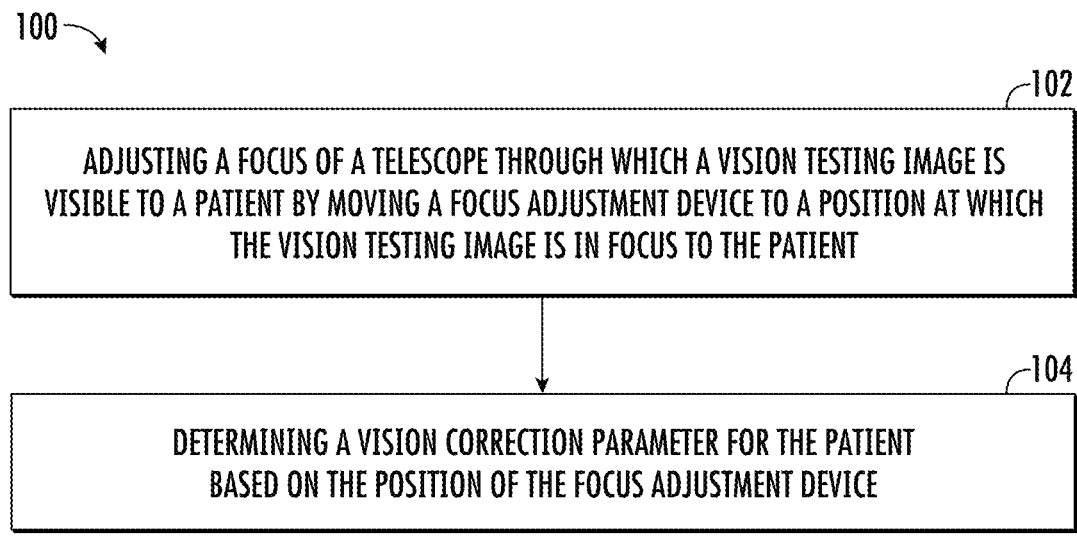
FIG. 1 is a flow diagram of an example of the telescopic ocular refraction test method.
FIG. 2 is a block diagram of an example of the telescopic ocular refraction test system.

This disclosure describes certain examples and features, but not all possible examples and features, of the telescopic ocular refraction test apparatus, system, and method. Where a particular feature is disclosed in the context of a particular example, that feature can also be used, to the extent possible, in combination with and/or in the context of other examples. The telescopic ocular refraction test apparatus, system, and method may be embodied in many different forms and should not be construed as limited to only the examples and features described here.

The telescopic ocular refraction test apparatus, system, and method give low vision patients the ability to choose the best subjective refractive corrective lenses by providing telescopic magnification of a vision testing image a fixed distance away from the patient.

The telescopic ocular refraction test apparatus, system, and method include or use a focusable telescope positioned in front of the patient's eye. The focusable telescope is calibrated for refractive error. A patient with reduced visual acuity will observe a vision testing image, and the telescope is focused until the magnified vision testing image appears clear to the patient.

The telescopic ocular refraction test system and apparatus may be manually operated or use electronics and software to provide analog and/or digital output as well as to connect to electronic medical record software.

The telescopic ocular refraction test apparatus, system, and method provide a monocular refractive correction of: sphere power, cylinder power, and/or cylinder axis. This provides a monocular refraction yielding corrective prescriptive lenses for hyperopia (far-sightedness), myopia (near-sightedness), astigmatic power, and axis of the astigmatism.

The telescopic ocular refraction test apparatus, system, and method can also be implemented binocularly to provide binocular refractive correction of sphere power, cylinder power, and/or cylinder axis, and perform a binocular balance of the refraction between two eyes. Binocular balance is typically performed if a patient's two eyes have roughly equally correctable acuity. A binocular balance is performed as follows. Plus lens focus (approximately +0.75) is added to both telescopes while a patient looks through the respective telescopes with respective eyes. Binocularity is then disrupted. This can be accomplished using a vertical prism, such that the patient sees two charts. Alternatively, this can be accomplished using alternate occlusion of the patient's eyes. When looking at the chart, the patient is asked if one eye sees the chart more clearly than the other. If so, the patient is told to defocus the better-seeing eye until both images appeared equally blurred. The prism is then removed, enabling binocularity. Then, both telescopes are reduced in plus lens power until best acuity is achieved. The telescopic ocular refraction test apparatus, system, and method can also determine the near refractive error for the purpose of prescribing a near lens correction. This is done by determining the difference between the distance refractive correction and the dioptric power needed to improve the correct refraction for near vision.

The telescopic ocular refraction test apparatus, system, and method will enable ophthalmologists, optometrists, and refractive technicians to serve patients with a vision impairment by providing them with an accurate lens prescription and improved visual acuity. For example, a patient with 20/1000 uncorrected visual acuity may achieve 20/200 corrected visual acuity, a potentially life-changing improvement.

As used herein, the term "low vision" means the patient has 20/70 or lower uncorrected visual acuity.

An example of a telescopic ocular refraction test method 100 is now described by referring to FIG. 1. At block 102, a focus of a telescope through which a vision testing image is visible to a patient is adjusted. This is achieved by moving a focus adjustment device to a position at which the vision testing image is in focus to the patient. At block 104, a vision correction parameter is determined for the patient based on the position of the focus adjustment device. The vision correction parameter can be determined manually or with the aid of a computing device.

The telescopic ocular refraction test method 100 may be implemented manually and/or with the assistance of a computerized control system.

Referring to FIG. 2, an example of a telescopic ocular refraction test system 200 that can implement the telescopic ocular refraction test method 100 includes a control system 202, a display screen 204, and a telescope 206. The telescope 206 has a magnification 207. Magnification 207 of a telescope is the ratio between respective focal lengths of the objective lens and eyepiece. The magnification 207 may be 1 to 12 and may be positive or negative. In a particular example, the magnification 207 is 3 and is positive. The magnification 207 is generally related to a depth of focus of the telescope 206. A short depth of focus is desirable for some of the tests disclosed herein.

In the example shown, the control system 202 includes a computing device that includes a processor 210, a memory 212, an I/O interface 214, and a network adapter 216. These features may communicate with each other through a bus or wirelessly and may be located within a single device or be divided across multiple devices. In other examples, the control system 202 may not be electronic and/or may be manually operated.

An example of the processor 210 is a computer microprocessor such as one that includes one or more processing units such as a central processing unit (CPU) and a graphical processing unit (GPU). The control system 202 may include one or more of the processors 210. In some cases, one or more of the processors 210 may be accessed remotely relative to one or more of the other processor(s) 210.

An example of the memory 212 includes non-transitory memory containing non-transitory computer executable program instructions. Examples of such memory 212 include a random-access memory (RAM), a hard disk, a removable storage device, or remote memory such as cloud storage.

The memory 212 stores data and executable program instructions, such as software programs, for performing various computing functions. The processor 210 is capable of executing the program instructions stored on memory 212 to cause the control system 202 to perform computing operations consistent with the apparatus, system, and method disclosed herein.

An example of the I/O interface 214 includes hardware and software for communication with the control system 202 by a user. The I/O interface 214 may include, for example, a keyboard, mouse, touch screen, camera, microphone, speaker, and/or the like.

An example of the network adapter 216 includes hardware and software for allowing the control system 202 to communicate information over a network. Examples of the network adapter 216 may include, for example, a local area network (LAN) adapter, a wireless wide area network (WWAN) adapter, a Bluetooth® module, a near field communication adapter, or the like.

The control system 202 is in wired and/or wireless communication with the display screen 204. The display screen 204 may be an electronic or non-electronic device. When the display screen 204 is an electronic device, it provides a visible output to a user and may be, for example, a television screen, a computer screen, an LCD screen, a headset screen, or the like. In this case, the control system 202 executes computer program instructions to electronically display the vision testing image 218 on the display screen 204. When the display screen 204 is a non-electronic device, the display screen 204 may be a board, paper, or the like having the vision testing image 218 thereon.

The telescopic ocular refraction test system 200 may be a plurality of independent components in communication or may be combined into an apparatus.

The telescopic ocular refraction test system 200 may be used to implement the telescopic ocular refraction test method 100 as now described.

In use, the control system 202 executes program instructions stored on the memory 212 to display the vision testing image 218 on the display screen 204. While the vision testing image 218 is being displayed on the display screen 204, a human patient 220 looks through the telescope 206 and views the vision testing image 218 through the telescope 206. The patient 220 is a distance 209 from the vision testing image 218, measured from the eye of the patient 220. The distance 209 may be five to thirty feet, five to twenty feet, ten to fifteen feet, or ten feet. The telescope 206 magnifies the vision testing image 218 as it appears to the patient 220. If the patient 220 visually perceives the magnified vision testing image 218 as blurry, a focus adjustment device 208 adjusts the focus of the telescope 206 until the patient 220 reports being able to visually perceive the vision testing image 218 more clearly. The focus adjustment device 208 may, for example, be adjusted until the patient 220 reports the ideal position of the focus adjustment device 208, which provides the patient with the clearest, least blurry, highest visual acuity perception of the vision testing image 218.

The focus adjustment device 208 is configured to change the focus of the telescope 206. Although this is typically achieved by adjusting the distance between an eye piece lens and an objective lens, there are other focus adjustment mechanisms that can be used, including digital focusing, for example. The focus adjustment device 208 may be a dial, button, motor, lever, or any other mechanism for adjusting the focus of the telescope 206. The focus adjustment device 208 may be adjusted manually by the patient 220 or a medical professional or automatically in response to an input signal from the control system 202.

The telescope 206 may be a Galilean or a Keplerian telescope. In certain examples of the telescopic ocular refraction test method 100, the telescope 206 is held by the patient 220 or medical staff during the test. In other examples, the telescope 206 is held in place by a mounting bracket that fixes the position of the telescope 206 relative to the display screen 204.

In a typical test, the patient 220 will have one eye covered while looking at the vision testing image 218 through the telescope 206. It may not always be necessary, however, for the patient 220 to have one eye covered.

Figure 3:
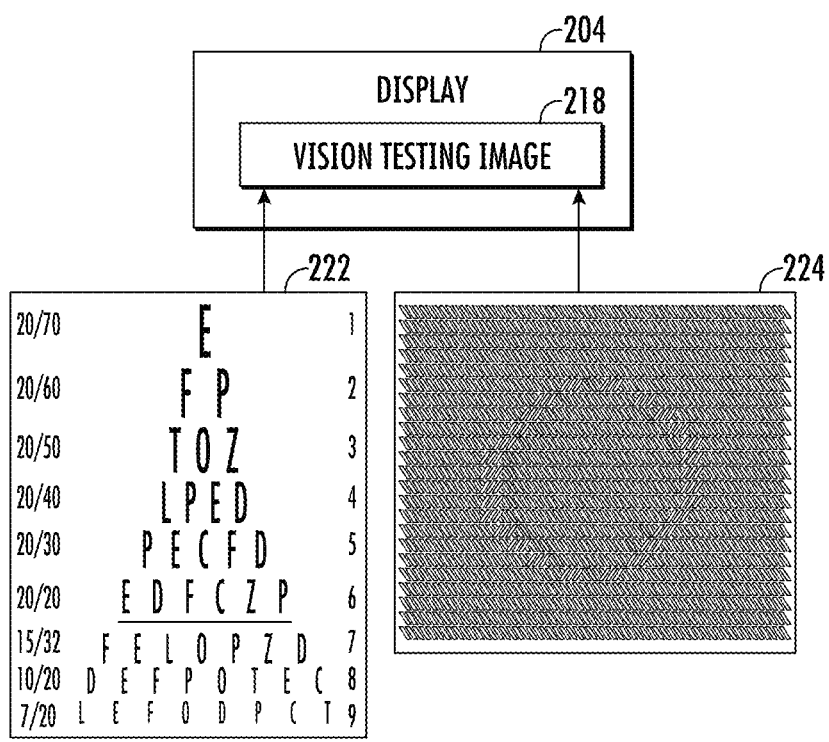
FIG. 3 is a block diagram of certain examples of the vision testing image.

Referring to FIG. 3, certain examples of the vision testing image 218 are now described. The vision testing image 218 is an image on the display screen 204 configured to permit vision testing.

One example of the vision testing image 218 is a visual acuity chart 222. The visual acuity chart 222 is a chart used to identify the smallest optotype a person can reliably identify. Examples of the visual acuity chart 222 may include a Snellen chart, a logMAR chart, a Landolt C E chart, a Lea test, a Golovin-Sivtsev table, a Rosenbaum chart, and a Jaeger chart.

Figure 48:
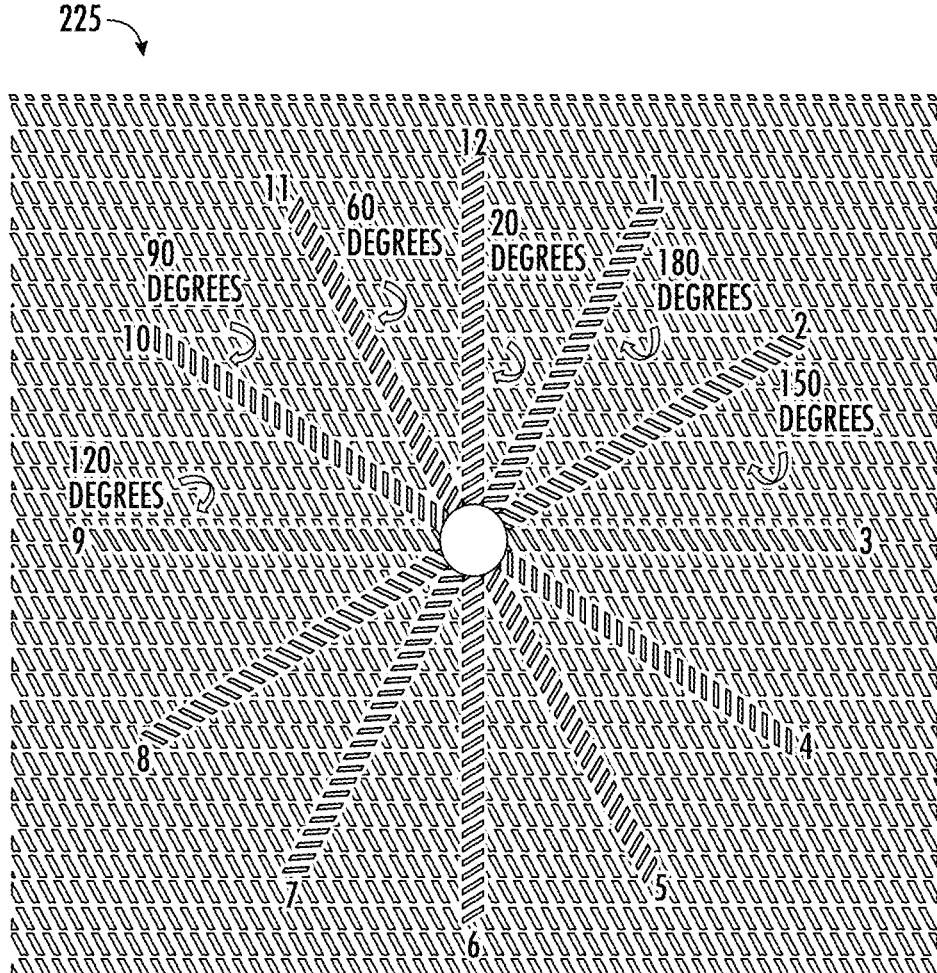
FIG. 48 is another example of a pattern frequency chart.

Another example of the vision testing image 218 is a pattern frequency chart 224, 225. A first example of a pattern frequency chart 224 is shown in FIG. 3. A second example of a pattern frequency chart 225 is shown in FIG. 48. Pattern frequency charts 224, 225 are designed to test the patient's 220 pattern frequency acuity. Pattern frequency charts 224, 225 operate on pattern receptors in the visual cortex that respond to lines and relationships of lines or patterns. The advantage of using a pattern frequency chart 224, 225 is it permits a response without the patient 220 needing to strain to see a detail or letter. This reduces over-correction, especially in the case of myopia. Certain other examples of a pattern frequency chart 224, 225 are described in International Publication No. WO 2024/006251.

Pattern frequency charts 224, 225 use pattern receptors to respond to the best resolution of detail. Pattern frequency charts 224, 225 are designed so that the image within the pattern can only be seen with the best corrected prescription power. They can also provide for assessment of cylinder power and axis of the cylinder to prescribe for astigmatism.

The vision testing image 218 is not limited to a visual acuity chart 222 or a pattern frequency chart 224, 225. Other conventional and unique charts or images that may be used to test visual acuity may also be used.

In a particular procedure, the patient 220 looks through the telescope 206 at the vision testing image 218, which is a distance 209 from the patient's 220 eye. In this example, the distance 209 is ten feet. The vision testing image 218 is a visual acuity chart 222 or a pattern frequency chart 224, 225. The focus adjustment device 208 is used to focus the telescope 206 until the vision testing image 218 appears in focus to the patient 220. The position at which the vision testing image 218 appears in focus is used to calculate the spherical equivalent vision correction parameter.

To calculate the cylinder axis and cylinder power vision correction parameters, the focus adjustment device 208 is used to bring the telescope out of focus, such that the vision testing image 218 is "blurred out," or no longer in focus. Once the spherical equivalent is determined, a pattern frequency chart 225 with sets of imbedded straight lines, such as that shown in FIG. 48, is presented as the vision testing image 218. The position of the focus adjustment device 208 is adjusted to a first position at which one set of lines appears darker or "blacker." This first position is used to calculate sphere power and cylinder axis. The position of the focus adjustment device 208 is further adjusted to a second position at which another set of lines appears darker or "blacker." The difference between the first position and the second position is used to calculate cylinder power.

Figure 4:
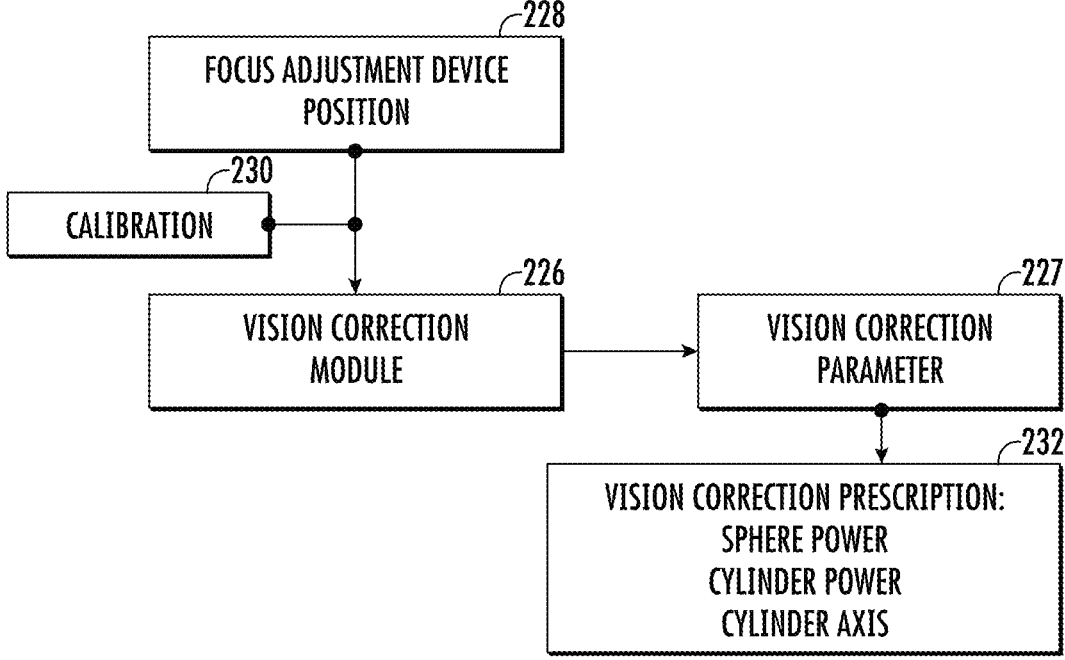
FIG. 4 is a block diagram of an example of the vision correction module.

Referring to FIG. 4, the memory 212 stores a vision correction module 226, which includes computer program instructions for determining a vision correction parameter 227 based on the position 228 of the focus adjustment device where the patient 220 reports having the clearest visual acuity perception of the vision testing image 218 through the telescope 206.

The control system 202 receives the focus adjustment device position 228 and provides it to the vision correction module 226. The vision correction module 226 uses a calibration 230 stored on the memory 212 to mathematically convert the focus adjustment device position 228 to the vision correction parameter 227. The calibration 230 is prepared prior to testing the patient 220 using the optical properties of the telescope 206 and quantitatively knowing how the focus adjustment device position 228 affects the focus of the telescope 206.

In another example, the calibration 230 is performed and the vision correction parameter 227 is printed on a label of the focus adjustment device 208 for manual determination of the vision correction parameter 227.

The vision correction parameter 227 is a parameter used in optometry to tell technicians the quantity of adjustment needed to correct a particular vision problem when making corrective lenses. Examples of vision correction parameters 227 include sphere power, cylinder power, and cylinder axis. The vision correction module 226 may also determine a vision correction prescription 232 for the patient 220 using the vision correction parameter(s) 227.

Figures 5, 6:
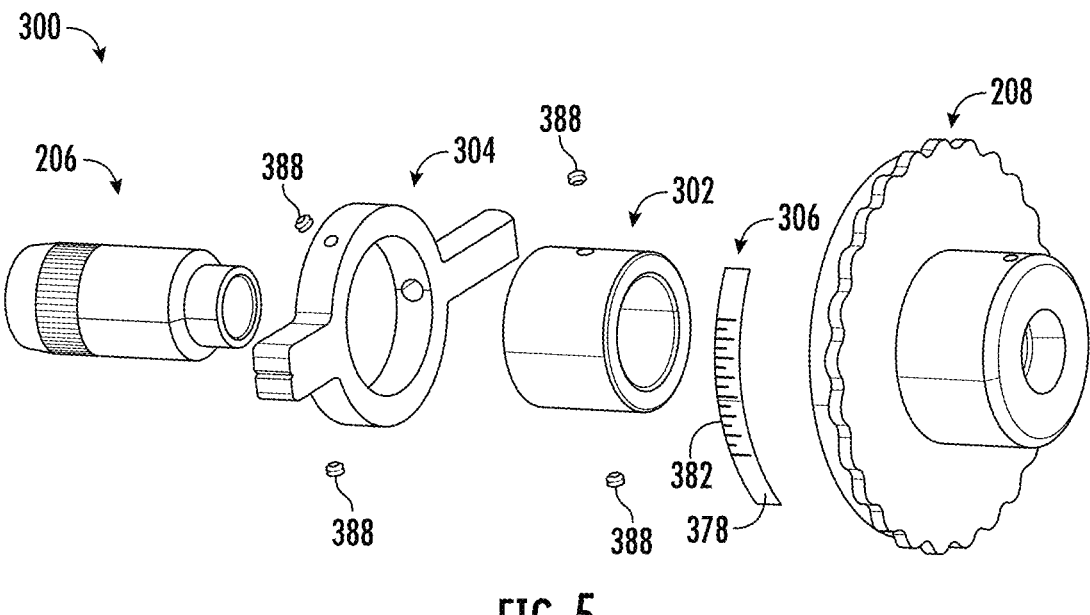
FIG. 5 is a perspective exploded view of an example of the telescopic ocular refraction test apparatus.
FIG. 6 is another perspective exploded view of the telescopic ocular refraction test apparatus of FIG. 5.
Figure 7:
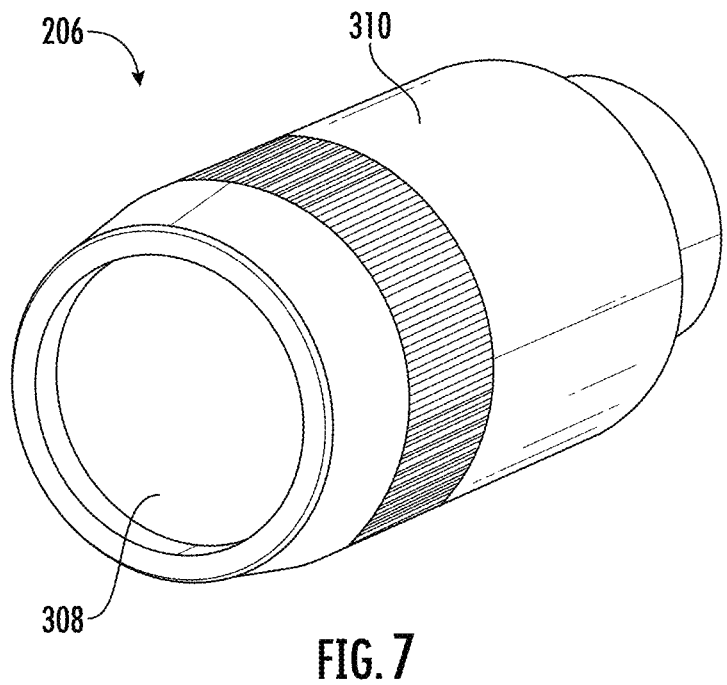
FIG. 7 is a front perspective view of an example of a telescope.
Figure 8:
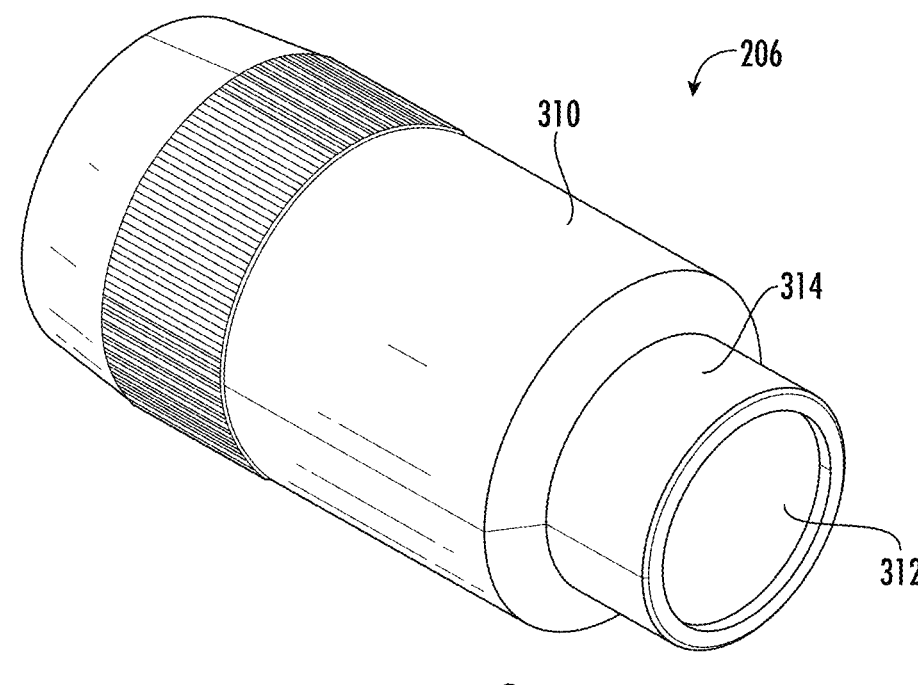
FIG. 8 is a rear perspective view of the telescope of FIG. 7.
Figure 12:
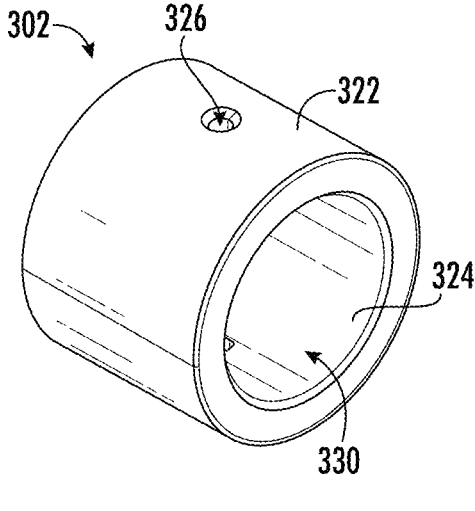
FIG. 12 is a front perspective view of an example of a support sleeve.
Figure 13:
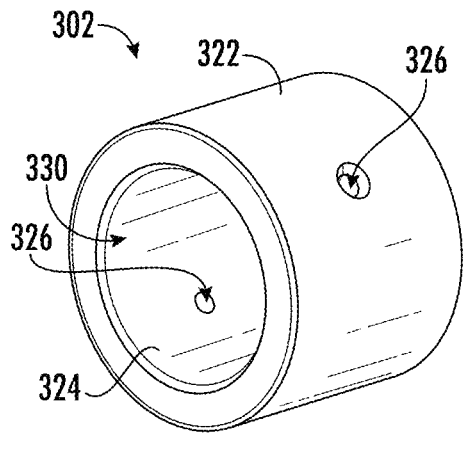
FIG. 13 is a rear perspective view of the support sleeve of FIG. 12.
Figure 14:
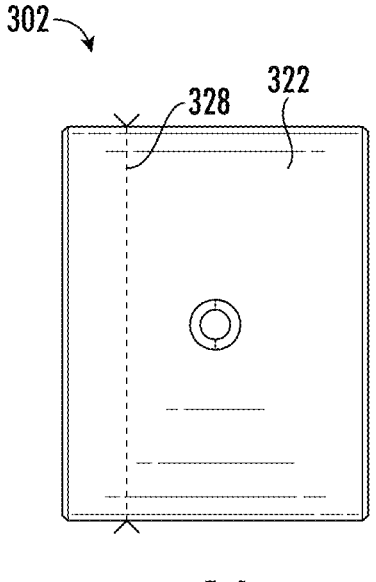
FIG. 14 is a top view of the support sleeve of FIG. 12, the bottom view being a mirror image.
Figure 15:
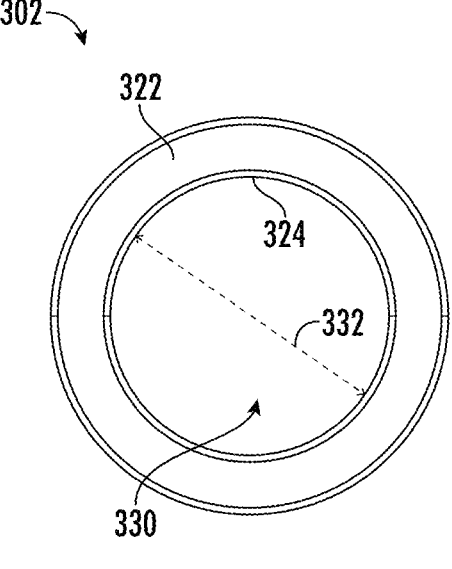
FIG. 15 is a front view of the example of the support sleeve.
Figure 16:
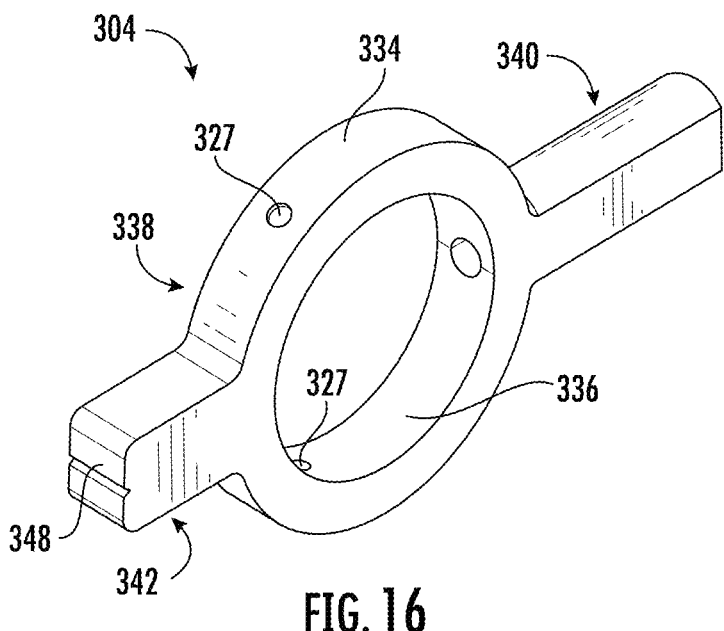
FIG. 16 is a perspective view of an example of a mounting bracket.
Figure 17:
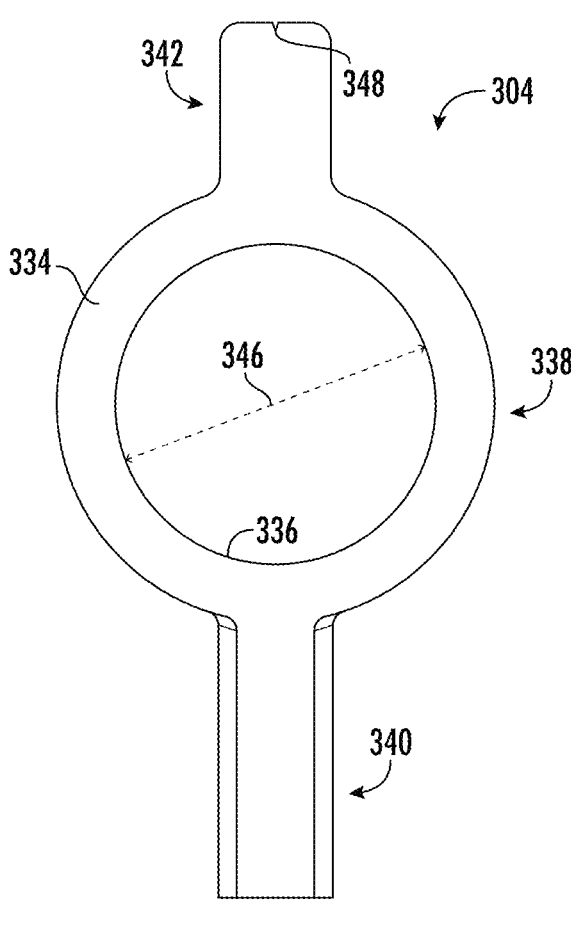
FIG. 17 is a front view of the mounting bracket of FIG. 16, the rear view being a mirror image.
Figures 18, 19:
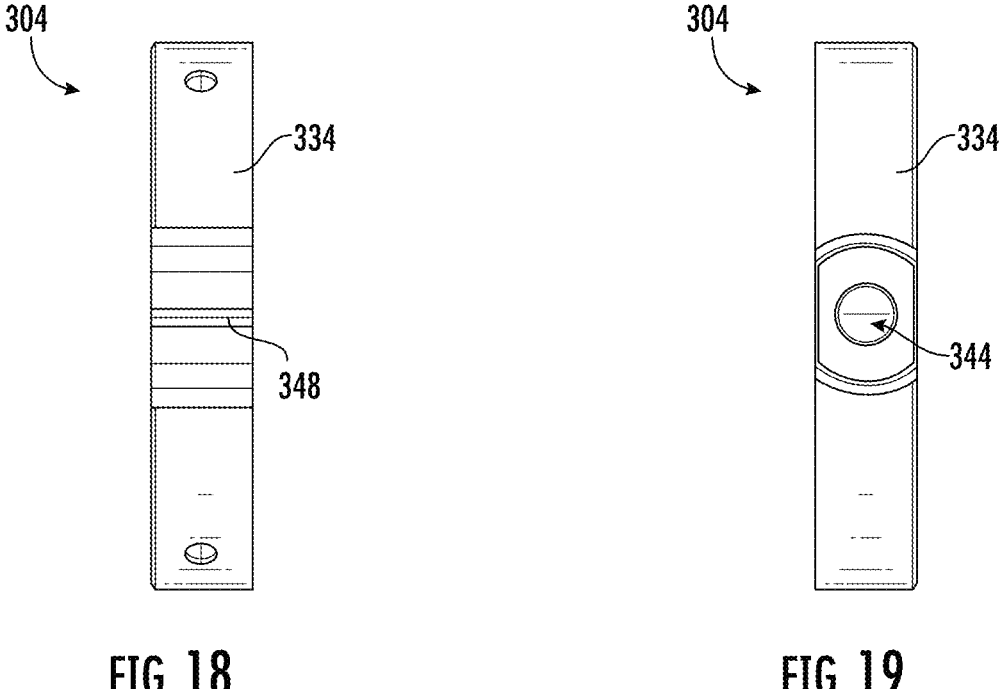
FIG. 18 is a top view of the mounting bracket of FIG. 16.
FIG. 19 is a bottom view of the mounting bracket of FIG. 16.
Figure 20:
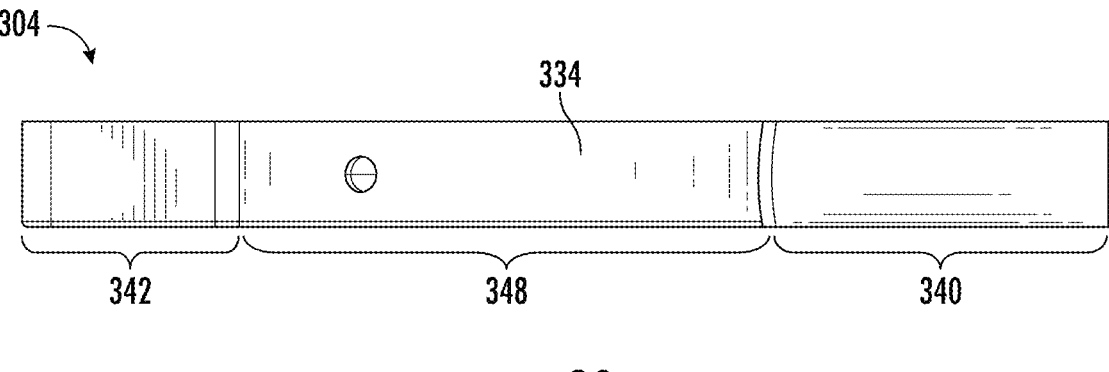
FIG. 20 is a right side view of the mounting bracket of FIG. 16, the left side view being a mirror image.

Referring to FIGS. 5-6, an example of a telescopic ocular refraction test apparatus 300 includes a telescope 206, a support sleeve 302, a mounting bracket 304, a focus adjustment device 208, and a label 306.

Referring to FIGS. 7-11, the telescope 206 has an eyepiece lens 312 with an eyepiece lens housing 314 and an objective lens 308 with an objective lens housing 310. The eyepiece lens housing 314 has an eyepiece lens housing diameter 318. The objective lens housing 310 has an objective lens housing diameter 316. The eyepiece lens housing 314 and objective lens housing 310 are adjustably connected such that a distance 320 between the eyepiece lens housing 314 and the objective lens housing 310 can be changed. Adjusting the distance 320 can be implemented to focus the telescope 206.

The eyepiece lens housing 314 and objective lens housing 310 are rotatably connected via a screw mechanism, a sliding mechanism, or another mechanism that permits the distance 320 to be adjusted.

Referring to FIGS. 12-15, the support sleeve 302 is a hollow cylinder with a support sleeve exterior surface 322 and a support sleeve interior surface 324. The support sleeve exterior surface 322 and support sleeve interior surface 324 define two opposing screw holes 326. The support sleeve exterior surface 322 defines a support sleeve outer diameter 328. The support sleeve interior surface 324 defines a cylindrical volume 330 with an inner diameter 332. The inner diameter 332 of the support sleeve 302 approximates the objective lens housing diameter 316. The support sleeve 302 is configured to fit around the objective lens housing 310 such that the objective lens housing 310 is within the cylindrical volume 330.

Referring to FIGS. 16-20, the mounting bracket 304 has a mounting bracket exterior surface 334 and a mounting bracket interior surface 336. The mounting bracket exterior surface 334 defines an annular body 338, a leg 340, and an indicator 342. The mounting bracket exterior surface 334 and mounting bracket interior surface 336 define two screw holes 326 and a mounting tube 344. The mounting bracket interior surface 336 defines an inner diameter 346. The inner diameter 346 approximates the support sleeve outer diameter 328.

The mounting bracket 304 is used to fix the position of the telescopic ocular refraction test apparatus 300 relative to the display screen 204 by connecting the leg 340 to a fixed object such as an examination chair, examination table, or other piece of fixed equipment. The leg 340 and indicator 342 extend radially outward from the annular body 338 in opposing directions. The mounting tube 344 extends from the mounting bracket interior surface 336 and entirely through the leg 340. In use, the leg 340 is secured to a table or other fixed structure, sometimes via a screw extending into the mounting tube 344 and mating with threads in the mounting tube 344. The indicator 342 has a groove 348 which serves as a reference point when observing a relative position of the focus adjustment device 208 to assist with identifying the position of the focus adjustment device 208.

Referring to FIGS. 21-33, in certain examples, the mounting bracket 304 is used to fix the ocular refraction test apparatus 300 to a chin rest assembly 500. The chin rest assembly 500 includes a stand 502, a frame 504, a chin rest 506, and a positioning assembly 508.

In the example shown, the stand 502 includes a stand frame 510 and a tripod 512 with three tripod legs 514. The stand frame 510 includes a lower plate 516 and an upper plate 518. The upper plate 518 defines four frame mounting holes 520. The tripod 512 is rotatably connected to the lower plate 516.

Figures 21, 22:
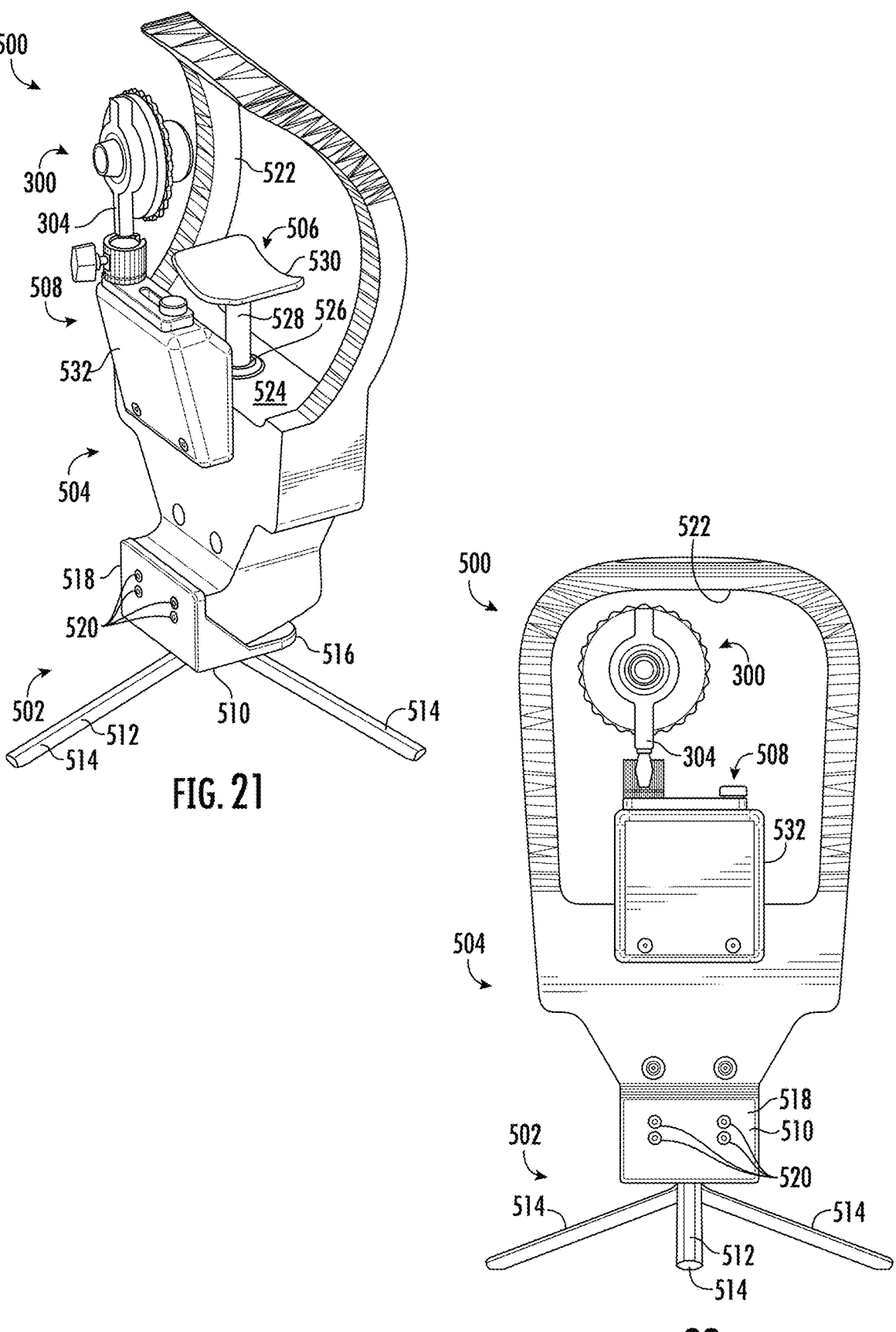
FIG. 21 is a front perspective view of the telescopic ocular refraction test apparatus of FIG. 5, installed on an example of a chin rest assembly.
FIG. 22 is a front view of the telescopic ocular refraction test apparatus of FIG. 5, installed on the chin rest assembly.
Figures 23, 24:
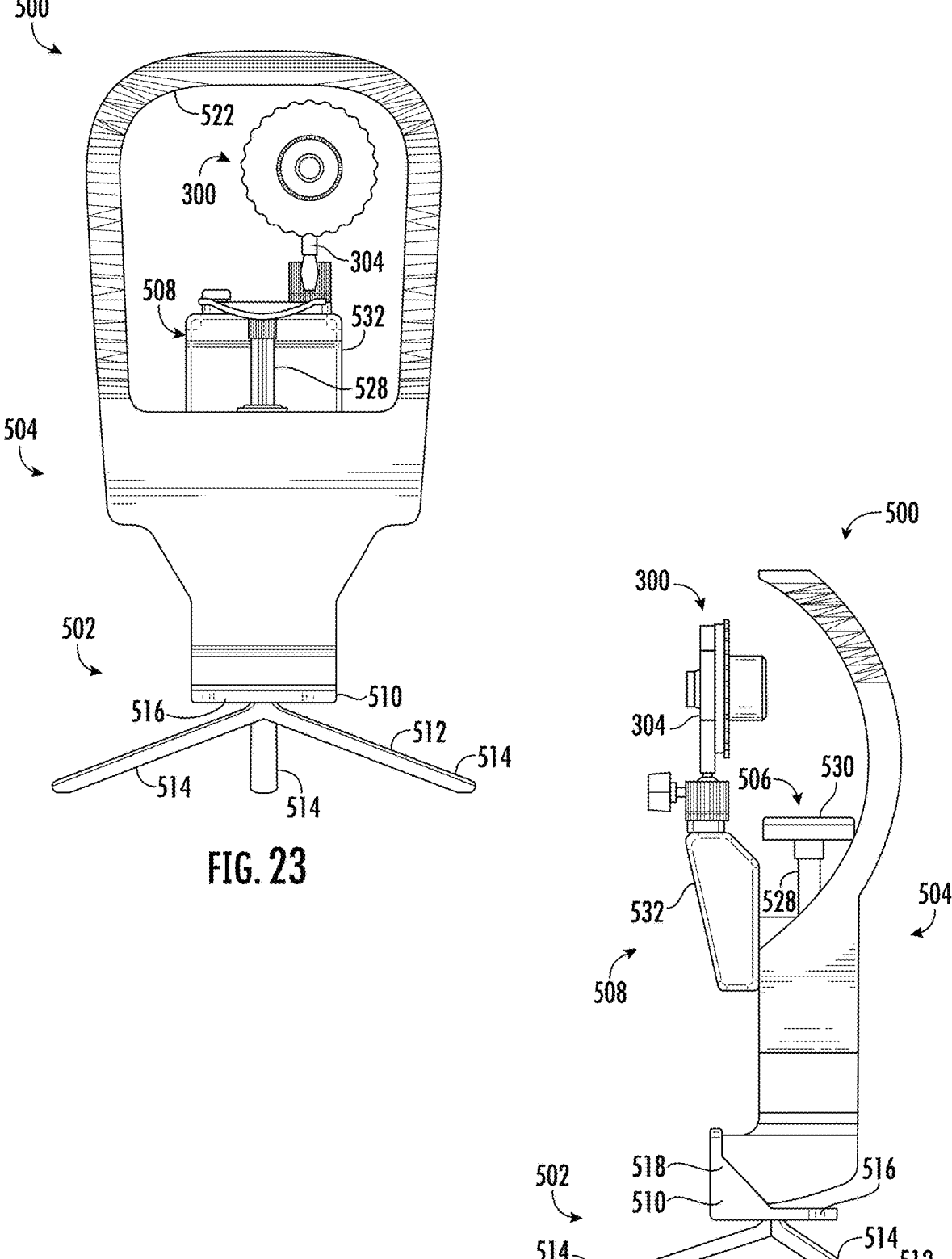
FIG. 23 is a rear view of the telescopic ocular refraction test apparatus of FIG. 5, installed on the chin rest assembly.
FIG. 24 is a right side view of the telescopic ocular refraction test apparatus of FIG. 5, installed on the chin rest assembly.
Figures 25, 26:
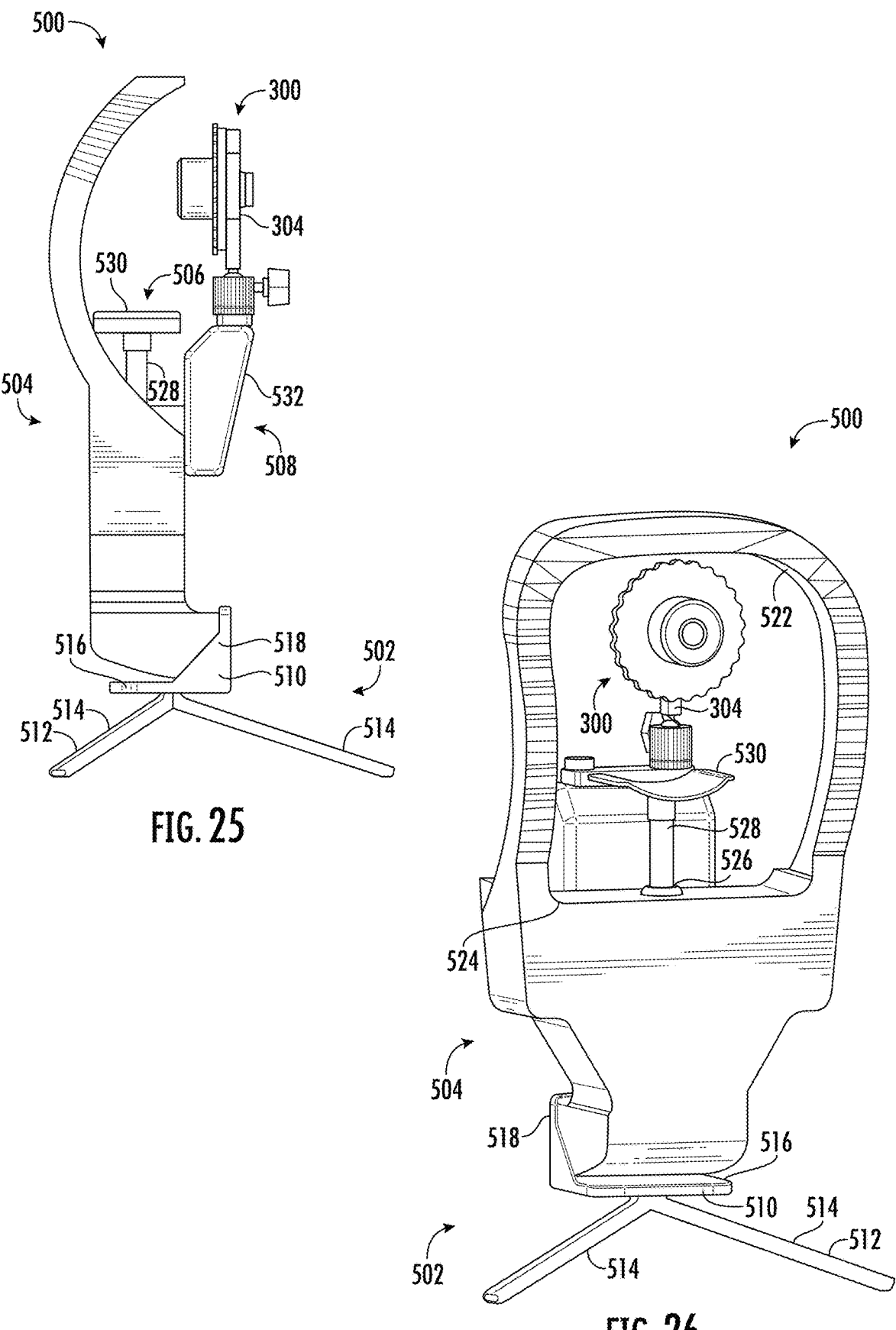
FIG. 25 is a left side view of the telescopic ocular refraction test apparatus of FIG. 5, installed on the chin rest assembly.
FIG. 26 is a rear perspective view of the telescopic ocular refraction test apparatus of FIG. 5, installed on the chin rest assembly.
Figure 27:
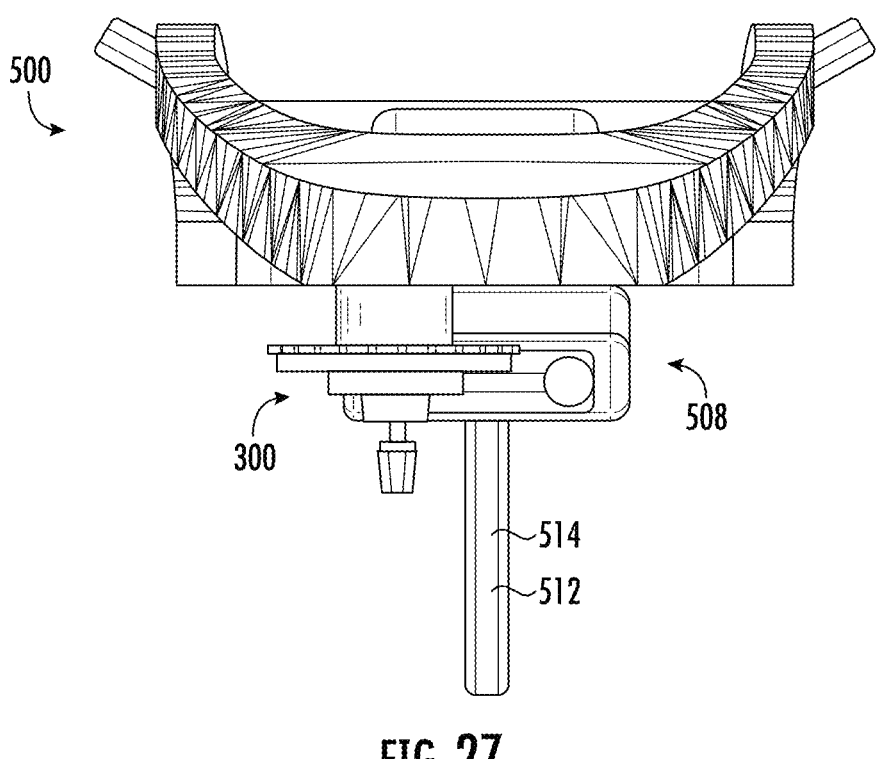
FIG. 27 is a top view of the telescopic ocular refraction test apparatus of FIG. 5, installed on the chin rest assembly.
Figure 28:
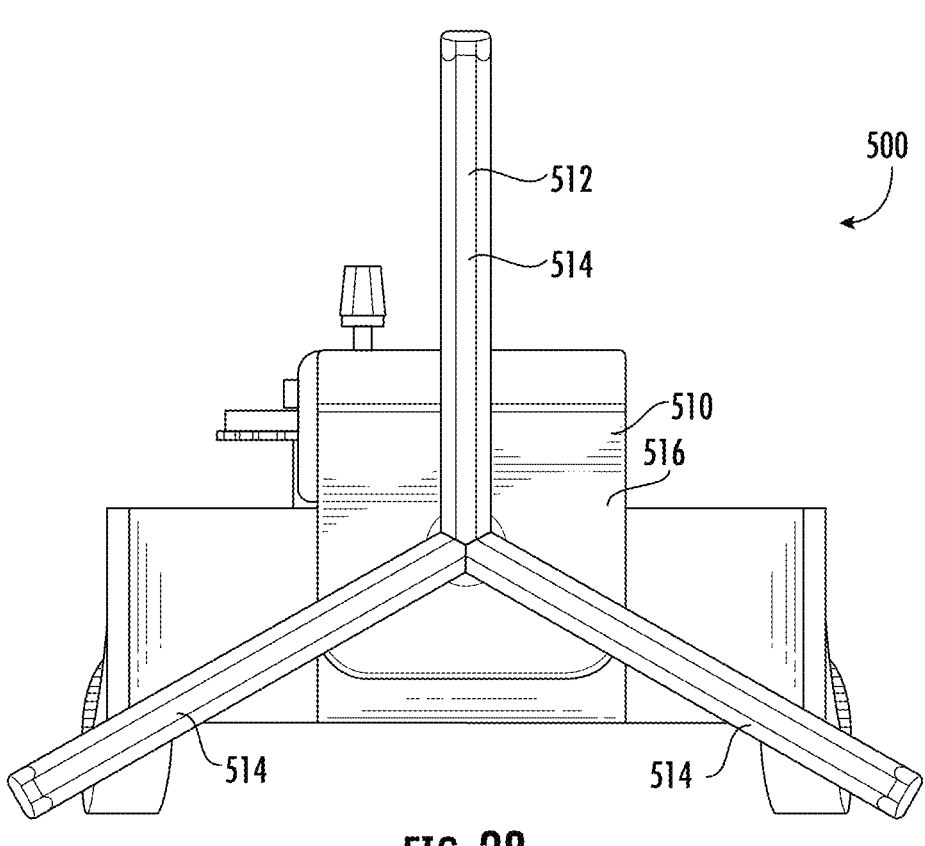
FIG. 28 is a bottom view of the telescopic ocular refraction test apparatus of FIG. 5, installed on the chin rest assembly.
Figure 30:
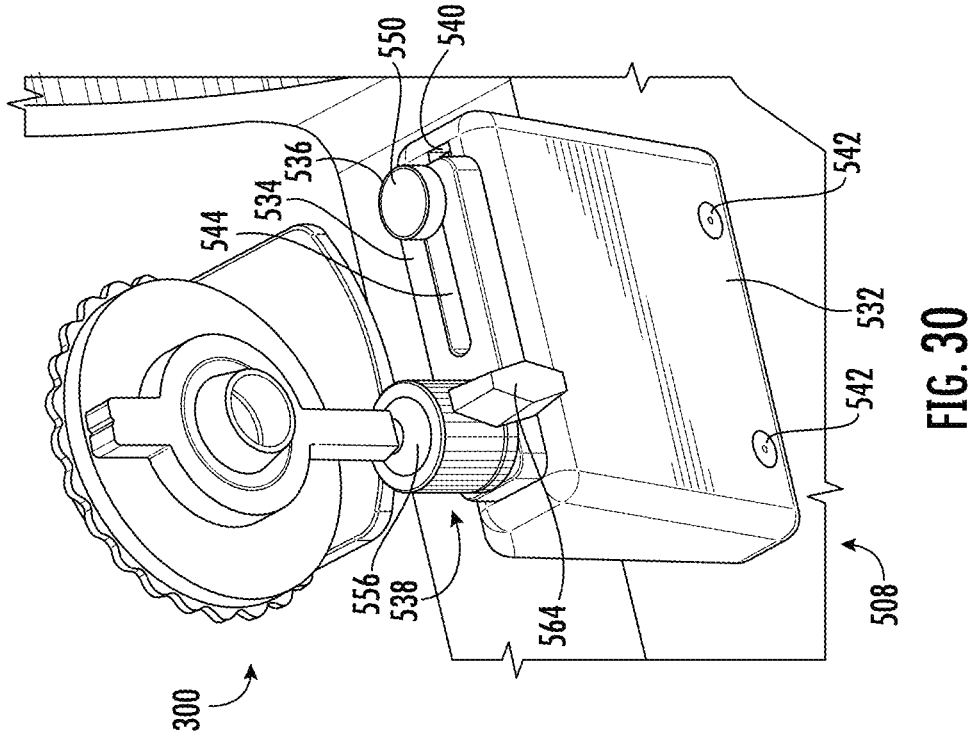
FIG. 30 is another front perspective, close-up view of the telescopic ocular refraction test apparatus of FIG. 5, installed on the positioning assembly.
Figure 29:
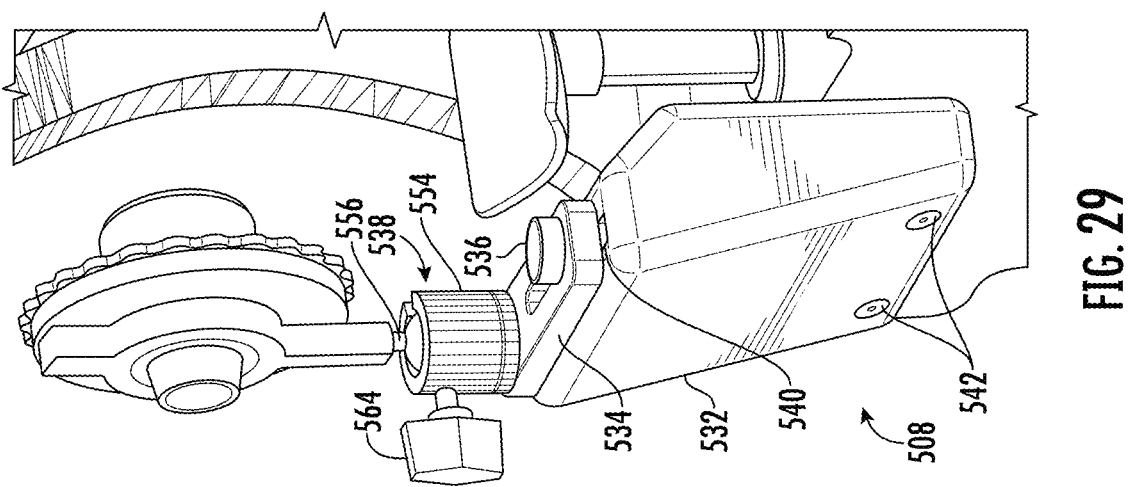
FIG. 29 is a front perspective, close-up view of the telescopic ocular refraction test apparatus of FIG. 5, installed on an example of a positioning assembly.

Referring in particular to FIG. 21, the frame 504 defines a window 522 with a chin rest mounting surface 524. The chin rest mounting surface 524 defines a chin rest hole 526.

The chin rest 506 includes a pillar 528 and a chin rest 530. The pillar 528 extends into the chin rest hole 526 such that the chin rest 530 extends above the chin rest mounting surface 524.

Referring in particular to FIGS. 29-33, the positioning assembly 508 includes an arm mount 532, an arm 534, a pivot 536, and a ball joint 538. The arm mount 532 defines a mount groove 540 and two arm mount holes 542. The arm 534 defines an arm slot 544 and an arm hole 546. The pivot 536 has a pivot head 548, a pivot washer 549, a pivot body 550, and a pivot nut 552. The ball joint 538 includes a socket 554 and a stud 556. The socket 554 defines a socket hole 558. The stud 556 includes a ball 560 and a connection member 562. A socket set screw 564 extends into the socket hole 558 and can be screwed in and out of the socket hole 558 such that it exerts a variable frictional force on the ball 560.

Figure 31:
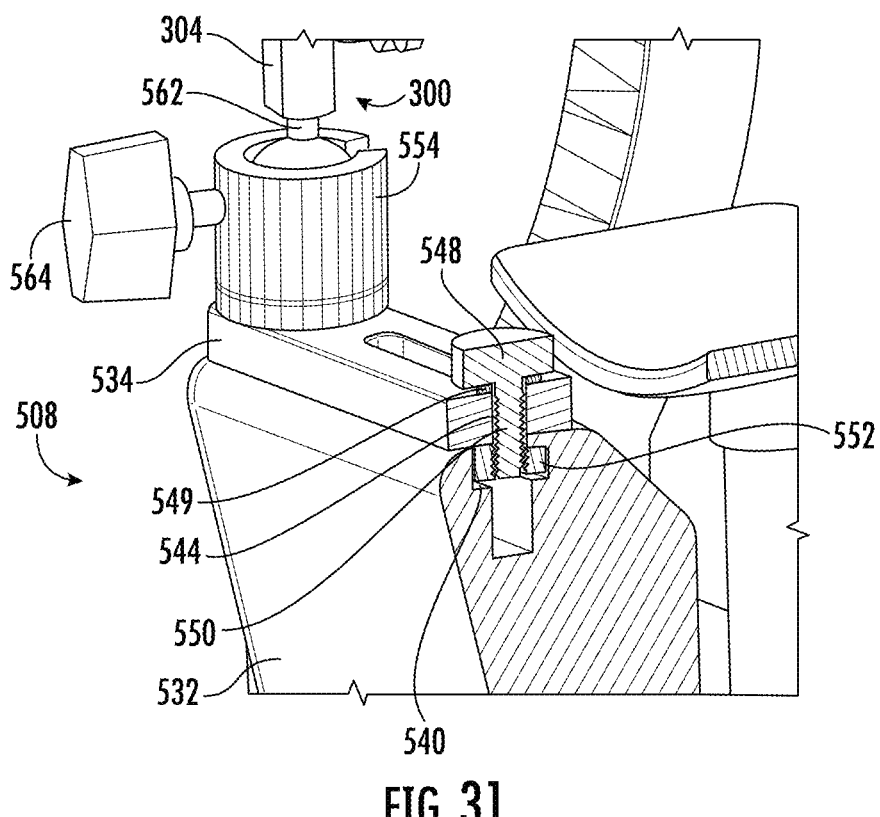
FIG. 31 is a cross-section, close-up view of the telescopic ocular refraction test apparatus of FIG. 5, installed on the positioning assembly.
Figure 32:
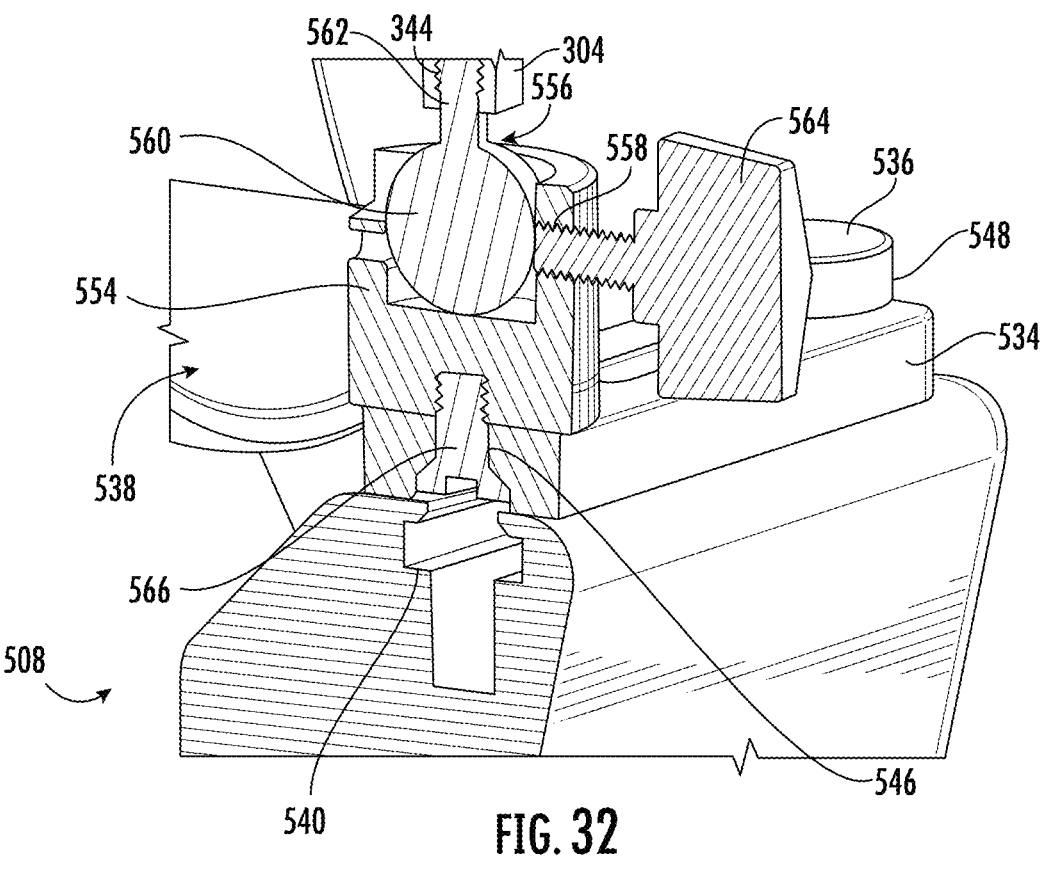
FIG. 32 is another cross-section, close-up view of the telescopic ocular refraction test apparatus of FIG. 5, installed on the positioning assembly.
Figure 33:
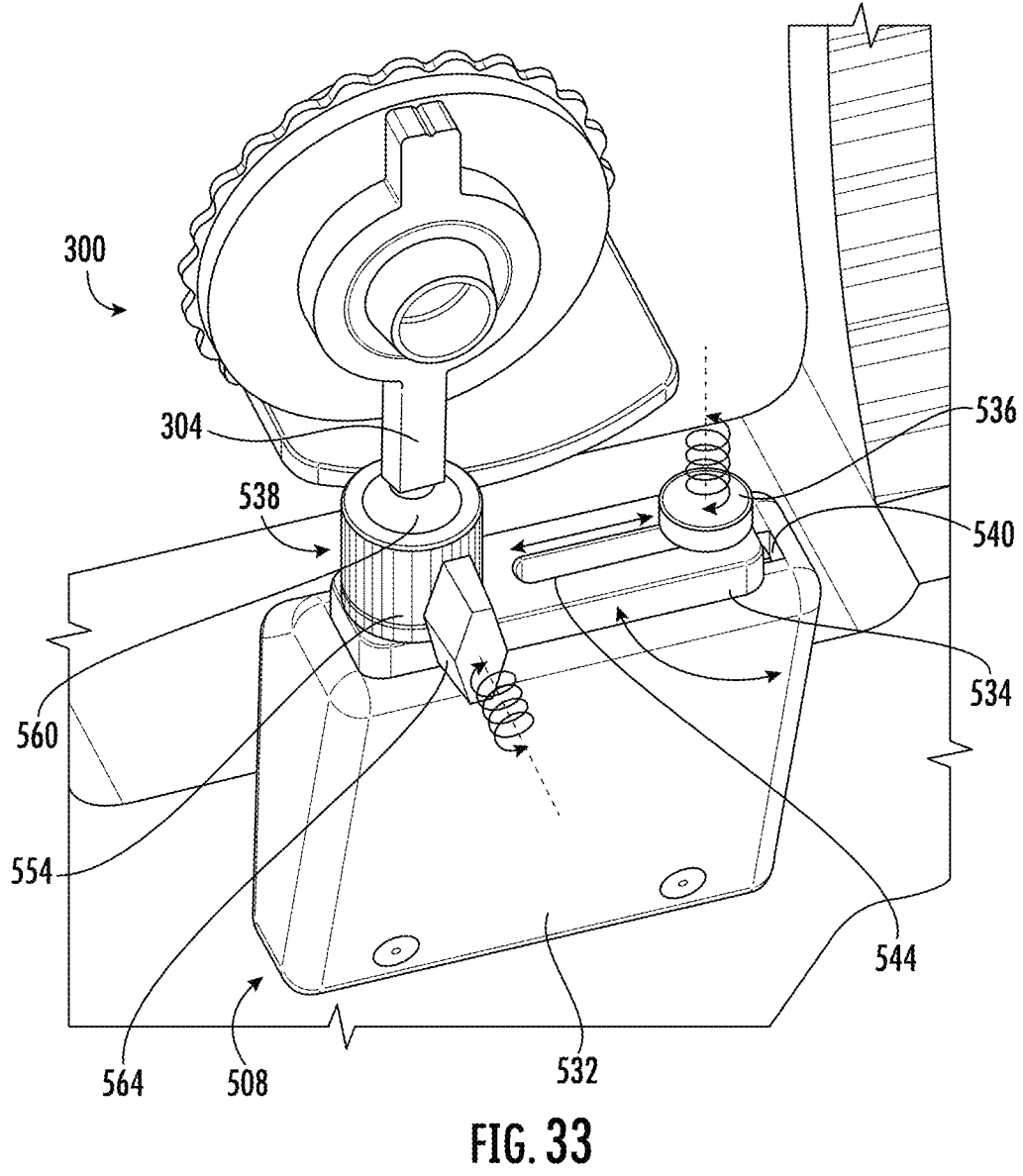
FIG. 33 is a top perspective, close-up view of the telescopic ocular refraction test apparatus of FIG. 5, installed on the positioning assembly, with arrows showing how different components can move.
Figure 34:
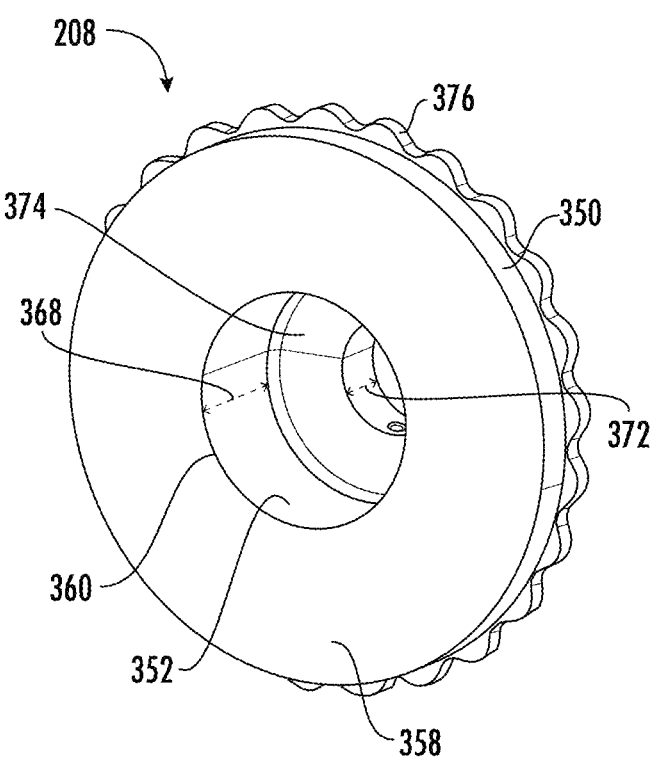
FIG. 34 is a front perspective view of an example of a focus adjustment device.
Figure 35:
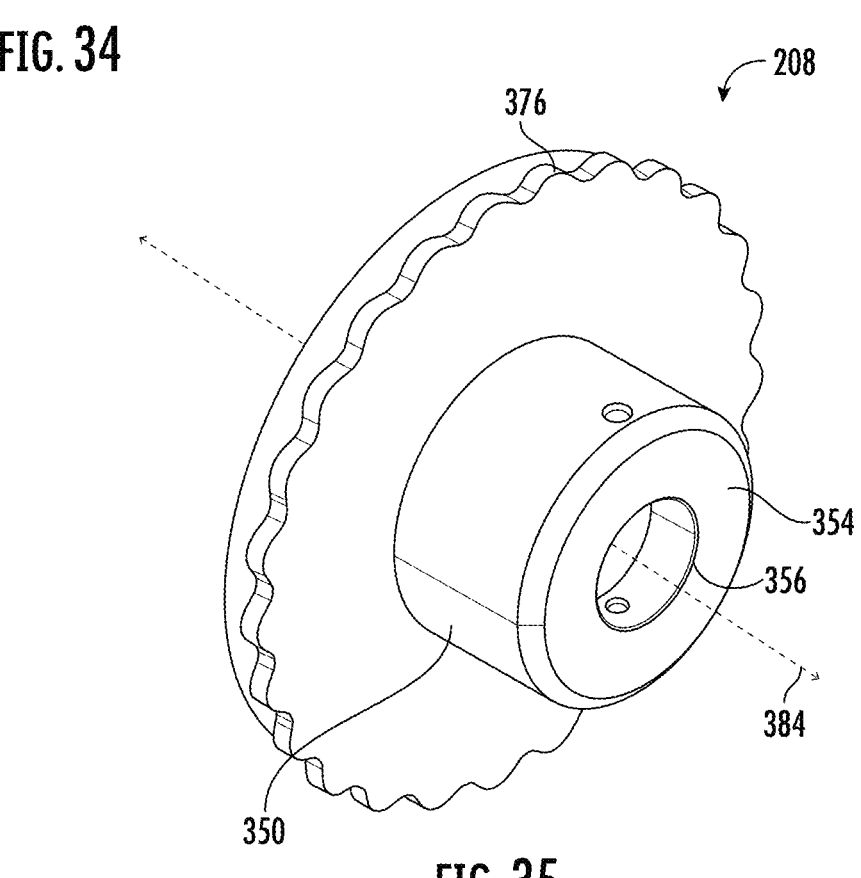
FIG. 35 is a rear perspective view of the focus adjustment device of FIG. 34.
Figures 36, 37:
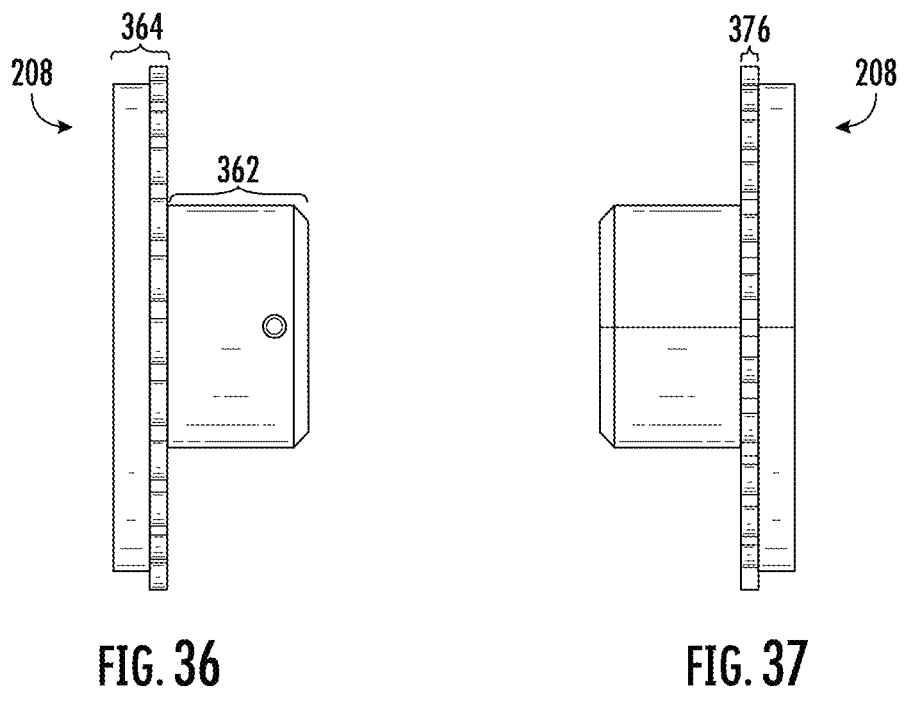
FIG. 36 is a right side view of the focus adjustment device of FIG. 34, the left side view being a mirror image.
FIG. 37 is a top view of the focus adjustment device of FIG. 34.
Figures 38, 39:
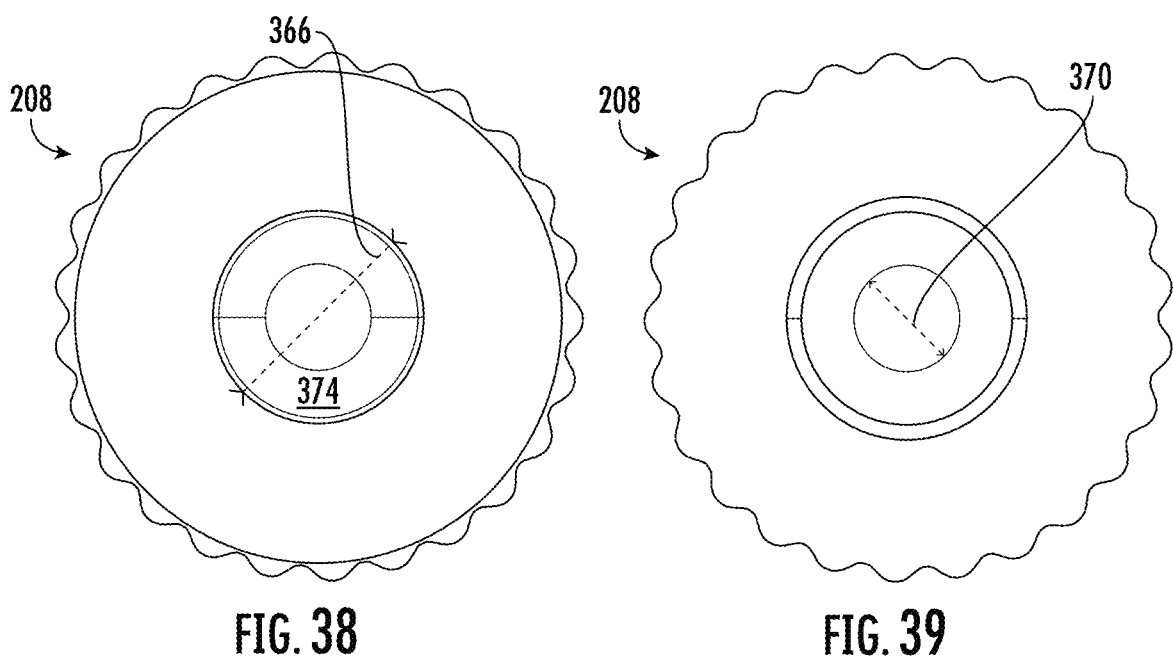
FIG. 38 is a front view of the focus adjustment device of FIG. 34.
FIG. 39 is a rear view of the focus adjustment device of FIG. 34.
Figures 40, 41:
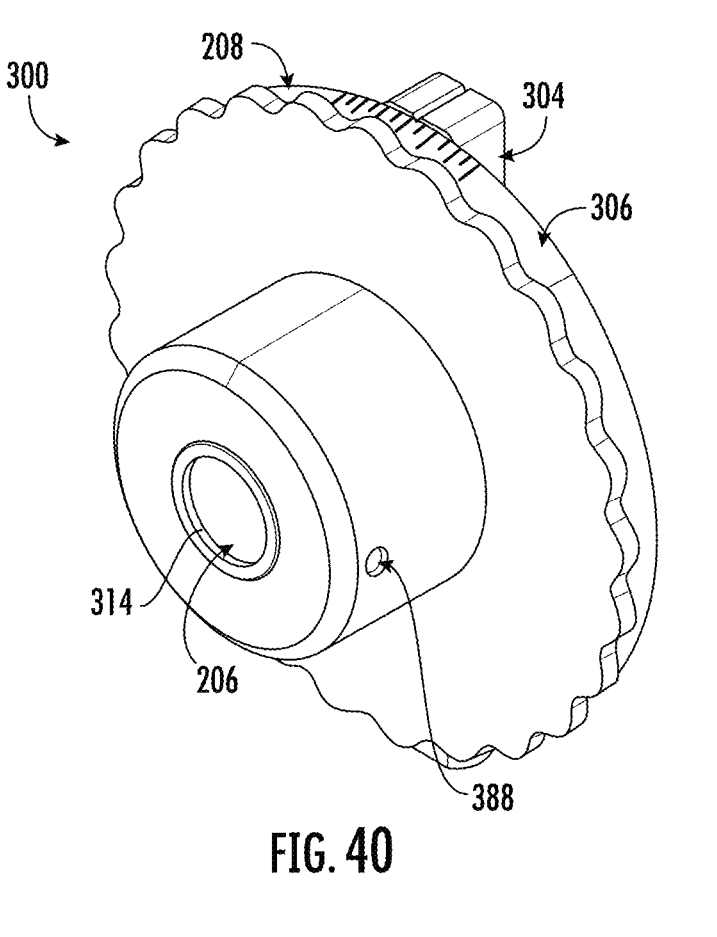
FIG. 40 is a rear perspective view of the telescopic ocular refraction test apparatus of FIG. 5.
FIG. 41 is a front perspective view of the telescopic ocular refraction test apparatus of FIG. 40.
Figures 42, 43:
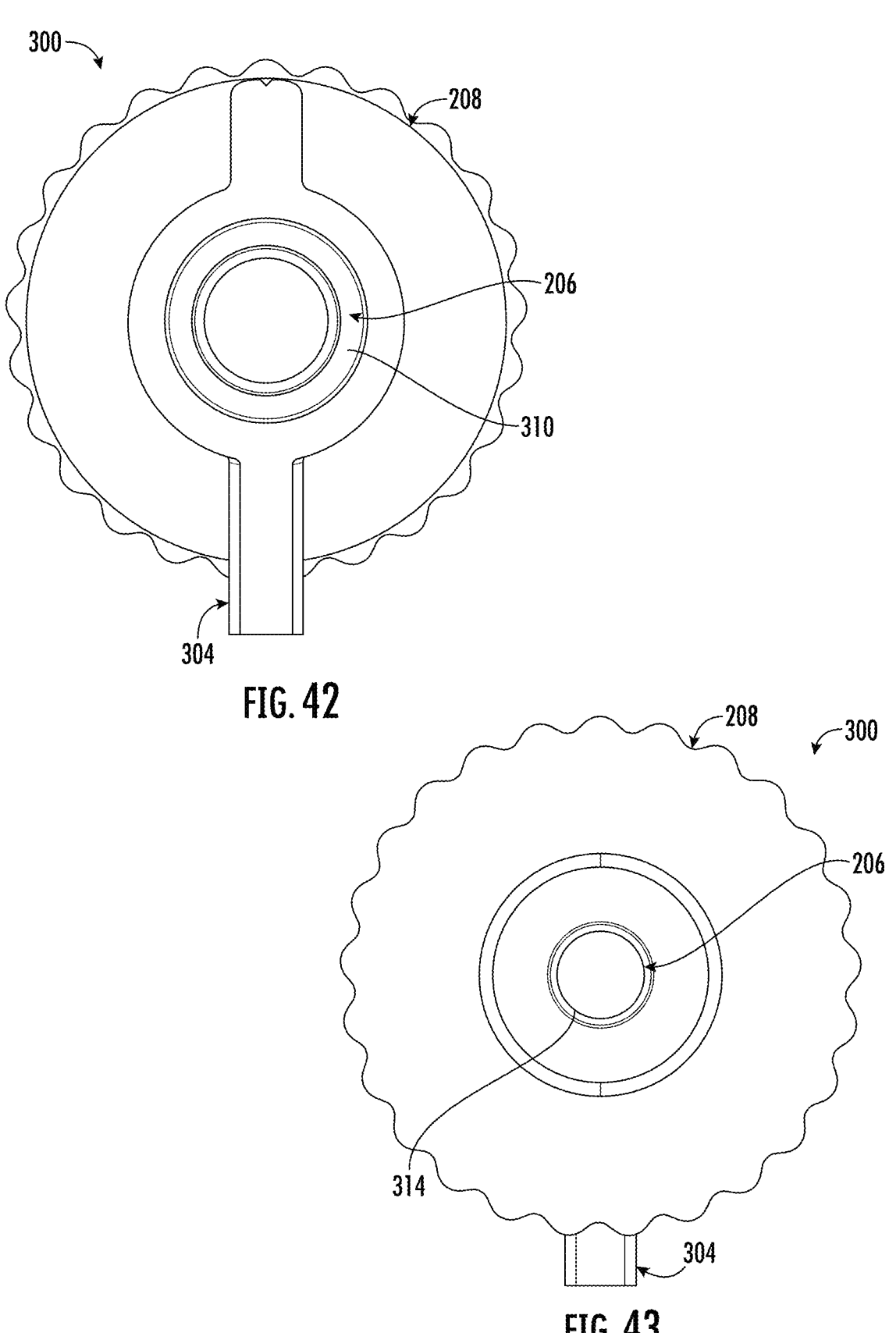
FIG. 42 is a front view of the telescopic ocular refraction test apparatus of FIG. 40.
FIG. 43 is a rear view of the telescopic ocular refraction test apparatus of FIG. 40.
Figure 44:
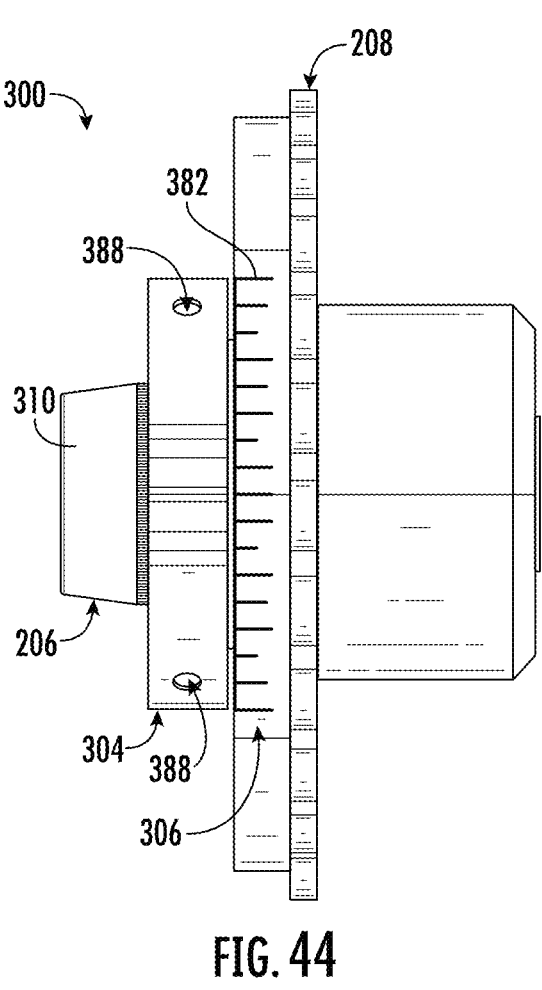
FIG. 44 is a top view of the telescopic ocular refraction test apparatus of FIG. 40.
Figure 45:
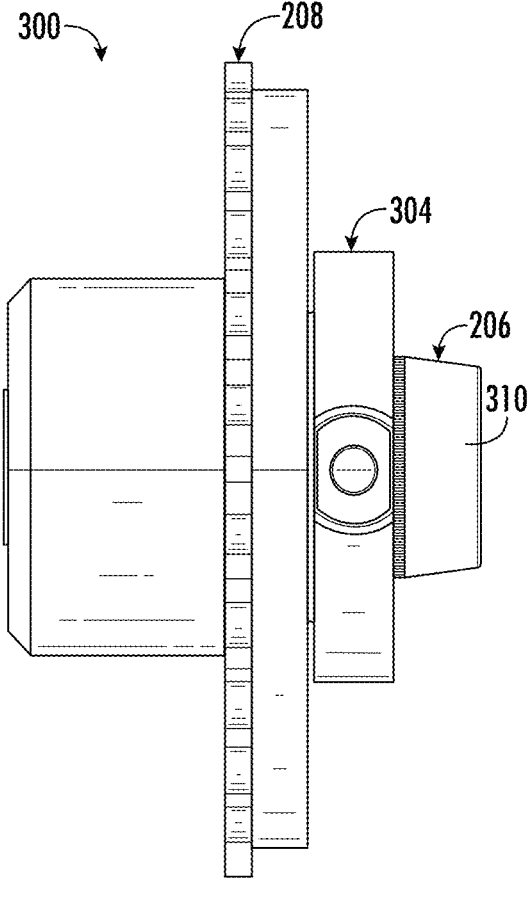
FIG. 45 is a bottom view of the telescopic ocular refraction test apparatus of FIG. 40.
Figures 46, 47:
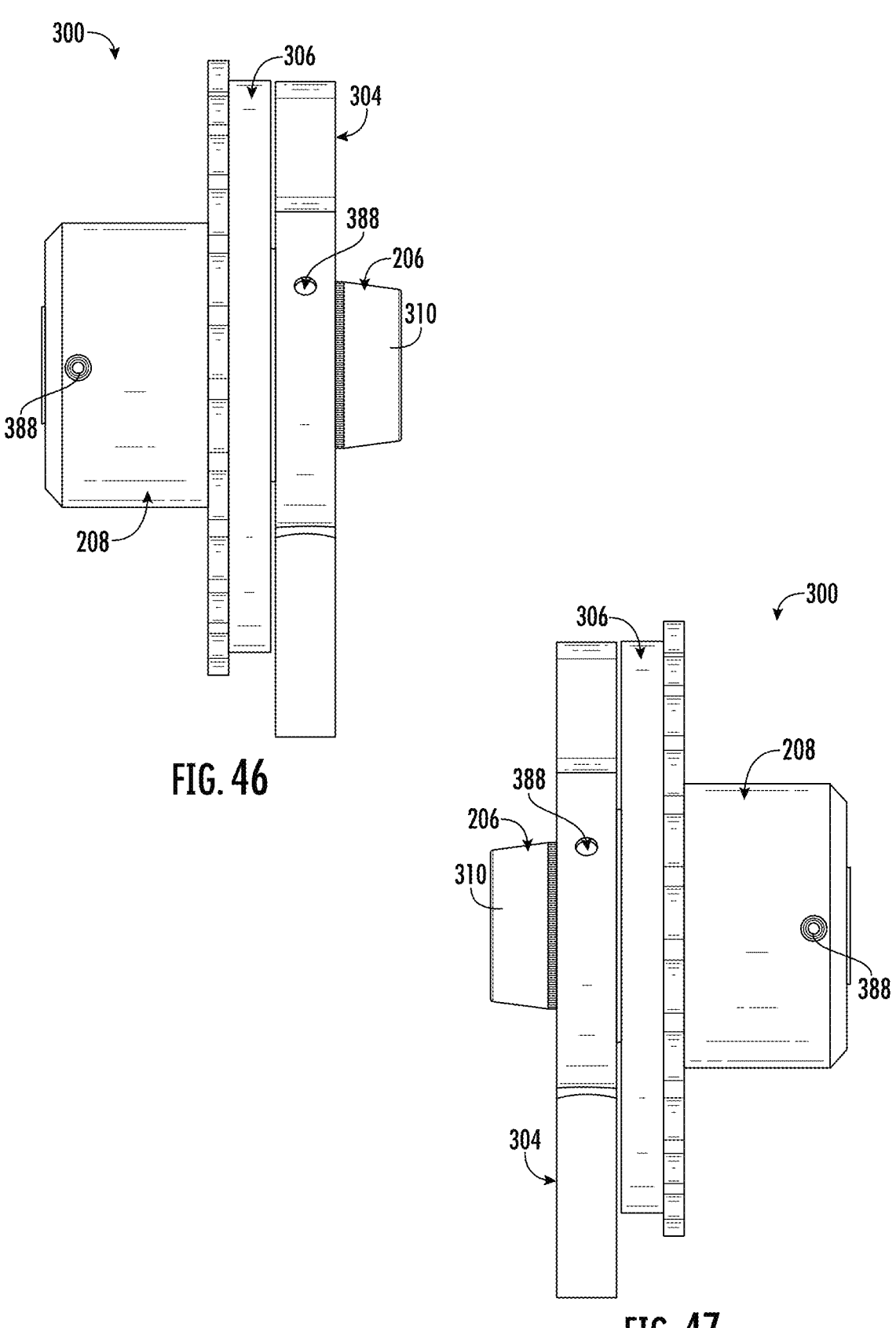
FIG. 46 is a left side view of the telescopic ocular refraction test apparatus of FIG. 40.
FIG. 47 is a right side view of the telescopic ocular refraction test apparatus of FIG. 40.

Referring now to FIGS. 31-33, the pivot nut 552 fits within the mount groove 540 and can be slidably positioned within the mount groove 540. The pivot body 550 extends through the arm slot 544 and can be slidably positioned within the arm slot 544. The arm 534 can also be rotated about the pivot 536. The pivot washer 549 is between the pivot head 548 and the arm 534. The arm 534 is between the pivot washer 549 and the arm mount 532 such that the pivot 536 adjustably connects the arm 534 to the arm mount 532. The socket 554 of the ball joint 538 is attached to the arm 534 via an arm screw 566 extending through the arm hole 546 and mating with the socket 554. The ball 560 fits within the socket 554 and can be adjustably positioned within the socket 554. The connection member 562 extends into the mounting tube 344 of the mounting bracket 304 to attach the telescopic ocular refraction test apparatus 300 to the positioning assembly 508.

When a patient 220 uses the telescopic ocular refraction test apparatus 300 attached to the positioning assembly 508, a chin of the patient 220 rests on the chin rest 530. The patient 220 looks through the window 522. Referring in particular to FIG. 33, the telescopic ocular refraction test apparatus 300 is positioned in front of an eye of the patient 220 by performing one or more of the following: slidably positioning the pivot nut 552 within the mount groove 540; slidably positioning the pivot body 550 within the arm slot 544; rotating the arm 534 about the pivot 536; and adjustably positioning the ball 560 within the socket 554. The socket set screw 564 may be screwed into the socket hole 558 to exert a frictional force on the ball 560 and hold the ball 560 stationary within the socket 554.

Referring to FIGS. 34-39, the focus adjustment device 208 has an exterior surface 350, an interior surface 352, a front face 358 defining a front aperture 360, and a rear face 354 defining a rear aperture 356. The interior surface 352 extends from the front aperture 360 to the rear aperture 356. The focus adjustment device 208 has a main body 362 and a flange 364.

The interior surface 352 defines a large diameter 366 extending through a radially enlarged portion 368 and a small diameter 370 extending through a radially constricted portion 372. The interior surface 352 defines an interior face 374 between the radially enlarged portion 368 and the radially constricted portion 372. The exterior surface 350 defines a texture 376 such as knurling on a radial periphery of the flange 364. The texture 376 provides a tactile portion of the focus adjustment device 208 to assist a user by increasing traction of the user's hand or fingers contacting the focus adjustment device 208. The texture 376 may extend to all or part of the flange 364, if desired.

The interior surface 352 and exterior surface 350 define two opposing screw holes 326 extending through the radially constricted portion 372. The large diameter 366 approximates the support sleeve outer diameter 328. The small diameter 370 approximates the eyepiece lens housing diameter 318. The radially enlarged portion 368 is configured to fit around the support sleeve 302, and the radially constricted portion 372 is configured to fit around the eyepiece lens housing 314.

Referring back to FIGS. 5-6, the label 306 has a first surface 378 and a second surface 380. The second surface 380 is configured to be placed on the exterior surface 350 of the focus adjustment device 208. The first surface 378 has indices 382 at predetermined intervals which may correspond, for example, to angular positions with respect to an axis 384 extending through the focus adjustment device 208. The second surface 380 may have an adhesive 386 on it. The label 306 works in conjunction with the groove 348 to assist with identifying the position of the focus adjustment device 208. The label 306 may display, for example, the vision correction parameter 227 such as the dioptric value of the spherical equivalent refractive correction.

Referring to FIGS. 40-47 the telescopic ocular refraction test apparatus 300 is assembled as it is in use. The objective lens housing 310 is positioned within the cylindrical volume 330 of the support sleeve 302. Screws 388 are screwed into the screw holes 326 of the support sleeve 302 to secure the support sleeve 302 to the objective lens housing 310. The support sleeve 302 is positioned within the radially enlarged portion 368 of the focus adjustment device 208. The eyepiece lens housing 314 fits within the radially constricted portion 372 of the focus adjustment device 208. Screws 388 are screwed into the screw holes 326 extending through the radially constricted portion 372 to secure the focus adjustment device 208 to the eyepiece lens housing 314. The mounting bracket 304 is positioned around the support sleeve 302. Screws 388 are screwed into the screw holes 326 of the mounting bracket 304 to secure the mounting bracket 304 to the support sleeve 302. The label 306 is on the exterior surface 350 of the focus adjustment device 208 on a portion of the flange 364 adjacent the texture 376 and the indicator 342.

Once the telescopic ocular refraction test apparatus 300 is assembled, the mounting bracket 304 holds the objective lens housing 310 fixed with respect to the display screen 204 and the eyepiece lens housing 314. Rotating the focus adjustment device 208 rotates the eyepiece lens housing 314 relative to the objective lens housing 310, allowing the telescope 206 to be focused by rotating the focus adjustment device 208. The label 306 moves with the focus adjustment device 208, relative to the groove 348 of the indicator 342, and facilitates identifying the position of the focus adjustment device 208 relative to the mounting bracket 304.

The telescopic ocular refraction apparatus, system, and method may be modified in many different ways without departing from the scope of what is claimed. The scope of the claims is not limited to only the particular features and examples described above.

That which is claimed is:

1. An ocular refraction test system comprising:
a display that displays a vision testing image;
a telescope configured to be positioned in front of an eye of a patient for viewing the vision testing image through the telescope; and
a control system that determines a vision correction parameter based on a position of a focus adjustment device that focuses the telescope;
wherein the vision correction parameter is at least one parameter selected from the group consisting of sphere power, cylinder power, and cylinder axis.

2. The ocular refraction test system of claim 1, wherein the vision testing image is a visual acuity chart.

3. The ocular refraction test system of claim 1, wherein the vision testing image is a pattern frequency chart.

4. The ocular refraction test system of claim 1, wherein the telescope is a Galilean telescope.

5. The ocular refraction test system of claim 1, wherein the telescope has a magnification of 1-12.

6. The ocular refraction test system of claim 1, wherein the eye of the patient is 5-30 feet from the vision testing image.

7. The ocular refraction test system of claim 1, wherein the focus adjustment device manually focuses the telescope.

8. The ocular refraction test system of claim 1, wherein the focus adjustment device automatically focuses the telescope in response to an input signal from the control system.

9. The ocular refraction test system of claim 1, wherein the position of the focus adjustment device is calibrated to correspond to a vision correction prescription.

10. The ocular refraction test system of claim 1, wherein the control system controls the position of the focus adjustment device in response to patient input and calculates a vision correction prescription for the patient based on the position at which the patient input corresponds to the patient having a highest acuity view of the vision testing image.

11. An ocular refraction test method comprising:
adjusting a focus of a telescope through which a vision testing image is visible to a patient by moving a focus adjustment device of the telescope to a position at which the vision testing image is in focus to the patient; and
determining a vision correction parameter for the patient based on the position of the focus adjustment device;
wherein the vision correction parameter is at least one parameter selected from the group consisting of sphere power, cylinder power, and cylinder axis.

12. The ocular refraction test method of claim 11, wherein the patient has 20/70 or lower uncorrected visual acuity.

13. The ocular refraction test method of claim 11, wherein the vision testing image is a visual acuity chart.

14. The ocular refraction test method of claim 11, wherein the vision testing image is a pattern frequency chart.

15. The ocular refraction test method of claim 11, wherein the telescope is a Galilean telescope.

16. The ocular refraction test method of claim 11, wherein the telescope has a magnification of 1-12.

17. The ocular refraction test method of claim 11, wherein an eye of the patient is 5-30 feet from the vision testing image.

18. The ocular refraction test method of claim 11, wherein moving the focus adjustment device includes automatically focusing the telescope in response to an input signal from a control system.

19. The ocular refraction test method of claim 11, wherein the position of the focus adjustment device is calibrated to correspond to a vision correction prescription.

20. The ocular refraction test method of claim 11, wherein a control system changes the position of the focus adjustment device in response to patient input and determines the vision correction parameter.

21. An ocular refraction test system comprising:
a telescope with a first end housing an eyepiece and a second end housing an objective lens;
a focus adjustment device that changes a distance between the eyepiece and objective lens to focus the telescope; and
a control system that converts a position of the focus adjustment device to a vision correction parameter for a patient that views a vision testing image through the telescope;
wherein the vision correction parameter is at least one parameter selected from the group consisting of sphere power, cylinder power, and cylinder axis.

22. The ocular refraction test system of claim 21, further comprising a display that displays the vision testing image, the vision testing image being a visual acuity chart and/or a pattern frequency chart.

23. The ocular refraction test system of claim 21, wherein the telescope is a Galilean telescope.

24. The ocular refraction test system of claim 21, wherein the telescope has a magnification of 1-12.

25. The ocular refraction test system of claim 21, wherein an eye of the patient is 5-30 feet from the vision testing image.

26. The ocular refraction test system of claim 21, wherein the focus adjustment device manually focuses the telescope.

27. The ocular refraction test system of claim 21, wherein the focus adjustment device automatically focuses the telescope in response to an input signal from the control system.

28. The ocular refraction test system of claim 21, wherein the position of the focus adjustment device is calibrated to correspond to a vision correction prescription.

29. The ocular refraction test system of claim 21, wherein the control system controls the position of the focus adjustment device in response to patient input and calculates a vision correction prescription for the patient based on the position at which the patient input corresponds to the patient having a highest acuity view of the vision testing image.

30. An ocular refraction test system comprising:
a display that displays a vision testing image;
a telescope configured to be positioned in front of an eye of a patient for viewing the vision testing image through the telescope; and
a control system that determines a vision correction parameter based on a position of a focus adjustment device that focuses the telescope;
wherein the control system controls the position of the focus adjustment device in response to patient input and calculates a vision correction prescription for the patient based on the position at which the patient input corresponds to the patient having a highest acuity view of the vision testing image.

31. The ocular refraction test system of claim 30, wherein the vision testing image is a visual acuity chart.

32. The ocular refraction test system of claim 30, wherein the vision testing image is a pattern frequency chart.

33. The ocular refraction test system of claim 30, wherein the vision correction parameter is at least one parameter selected from the group consisting of sphere power, cylinder power, and cylinder axis.

34. The ocular refraction test system of claim 30, wherein the telescope is a Galilean telescope.

35. The ocular refraction test system of claim 30, wherein the telescope has a magnification of 1-12.

36. The ocular refraction test system of claim 30, wherein the eye of the patient is 5-30 feet from the vision testing image.

37. The ocular refraction test system of claim 30, wherein the focus adjustment device manually focuses the telescope.

38. The ocular refraction test system of claim 30, wherein the focus adjustment device automatically focuses the telescope in response to an input signal from the control system.

39. The ocular refraction test system of claim 30, wherein the position of the focus adjustment device is calibrated to correspond to a vision correction prescription.

40. An ocular refraction test system comprising:
a telescope with a first end housing an eyepiece and a second end housing an objective lens;
a focus adjustment device that changes a distance between the eyepiece and objective lens to focus the telescope; and
a control system that converts a position of the focus adjustment device to a vision correction parameter for a patient that views a vision testing image through the telescope;
wherein the control system controls the position of the focus adjustment device in response to patient input and calculates a vision correction prescription for the patient based on the position at which the patient input corresponds to the patient having a highest acuity view of the vision testing image.

41. The ocular refraction test system of claim 40, further comprising a display that displays the vision testing image, the vision testing image being a visual acuity chart and/or a pattern frequency chart.

42. The ocular refraction test system of claim 40, wherein the vision correction parameter is at least one parameter selected from the group consisting of sphere power, cylinder power, and cylinder axis.

43. The ocular refraction test system of claim 40, wherein the telescope is a Galilean telescope.

44. The ocular refraction test system of claim 40, wherein the telescope has a magnification of 1-12.

45. The ocular refraction test system of claim 40, wherein an eye of the patient is 5-30 feet from the vision testing image.

46. The ocular refraction test system of claim 40, wherein the focus adjustment device manually focuses the telescope.

47. The ocular refraction test system of claim 40, wherein the focus adjustment device automatically focuses the telescope in response to an input signal from the control system.

48. The ocular refraction test system of claim 40, wherein the position of the focus adjustment device is calibrated to correspond to a vision correction prescription.

* * * * *